United States Patent [19]
Cote et al.

[11] Patent Number: 5,248,424
[45] Date of Patent: Sep. 28, 1993

[54] FRAMELESS ARRAY OF HOLLOW FIBER MEMBRANES AND METHOD OF MAINTAINING CLEAN FIBER SURFACES WHILE FILTERING A SUBSTRATE TO WITHDRAW A PERMEATE

[75] Inventors: Pierre L. Cote, Hamilto; Bradley M. Smith; Ake A. Deutschmann, both of Mississauga; Carlos F. F. Rodrigues, Brampton; Steven K. Pedersen, Burlington, all of Canada

[73] Assignee: Zenon Environmental Inc., Burlington, Canada

[21] Appl. No.: 977,601

[22] Filed: Nov. 17, 1992

Related U.S. Application Data

[63] Continuation-in-part of Ser. No. 845,168, Mar. 3, 1992, Pat. No. 5,182,019, which is a continuation-in-part of Ser. No. 569,405, Aug. 17, 1990, Pat. No. 5,104,535.

[51] Int. Cl.$^5$ .................. B01D 61/18; B01D 63/02
[52] U.S. Cl. .................. 210/636; 210/644; 210/321.69; 210/321.8; 210/321.89; 210/500.23
[58] Field of Search ............ 210/634, 636, 641, 644, 210/649-652, 321.69, 321.72, 321.78-321.81, 321.87-321.9, 500.23

[56] References Cited

FOREIGN PATENT DOCUMENTS 510328A 10/1992 European Pat. Off. .

OTHER PUBLICATIONS

"Direct Solid-Liquid Separation Using Hollow Fiber Membrane In an Activated Sludge Aeration Tank" by K. Yamamoto; M. Hiasa; T. Mahmood and T. Matsuo. Wat. Sci. Tech. vol. 21, Brighton, pp. 43-54 (1989).

Primary Examiner—Frank Sever
Attorney, Agent, or Firm—Alfred D. Lobo

[57] ABSTRACT

A frameless array unconfined in a modular shell, proves to be a surprisingly effective membrane device for withdrawing permeate from a substrate, the flux through the membranes reaching an essentially constant relatively high value because of the critical deployment of fibers of the array as a skein, arching in a buoyantly swayable generally parabolic configuration within the substrate, above at least one of the array's headers in which the terminal end portions of the fibers are potted. The length of each fiber must be greater than the direct center-to-center distance between the array's pair of headers. For use in a large reservoir, an assembly of the array and a gas distributor means has fibers preferably >0.5 meter long, which together provide a surface area >10 m$^2$. The terminal end portions of fibers in each header are substantially free from fiber-to-fiber contact. When used in a tank from which the permeate is withdrawn at a location low enough to overcome the transmembrane pressure differential of the fibers, the permeate is withdrawn under a vacuum induced by gravity. To increase flux, a pump may be used which provides a suction less than 75 cm of Hg. When used in combination with a gas-distribution manifold disposed beneath the skein so as to flow bubbles through it, the surfaces of the fibers are surprisingly resistant to being fouled by build-up of deposits of inanimate particles or microorganisms in the substrate. Membranes with high transmembrane pressure differential may be used, if desired, and permeate removed with a vacuum pump.

24 Claims, 16 Drawing Sheets

FRAMELESS ARRAY OF HOLLOW FIBER MEMBRANES AND METHOD OF MAINTAINING CLEAN FIBER SURFACES WHILE FILTERING A SUBSTRATE TO WITHDRAW A PERMEATE

BACKGROUND OF THE INVENTION

This invention is a continuation-in-part application of copending patent application Ser. No. 07/845,168 filed Mar. 3, 1992, now U.S. Pat. No. 5,182,019, which in turn is a copending patent application of Ser. No. 07/569,405 filed Aug. 17, 1990, issued as U.S. Pat. No. 5,104,535 on Apr. 14, 1992.

Our grandparent '405 application was directed to a frameless array of hollow fibers, which array was formed without potting the terminal portions of the fibers. The term "fibers" is used herein as it was in the grandparent, to refer to "hollow fiber membranes", for brevity. The term "array" was used therein to refer to a layer of plural fibers in spaced-apart relationship in a single plane. The fibers were held near their terminal portions in a pair of opposed identical split-clip headers which were displaceable in any direction relative to one another. The headers were provided with grooves in which ends of the fibers were secured. We referred to them as "split-clip" headers because the headers would eventually be "clipped" together (as in a clip of ammunition), in one form or another, before an assembly of arrays could be put to use.

Our parent '168 application was specifically described in relation to an assembly of frameless arrays sealingly bonded together along their borders, by postpotting, to form a cartridge for use in the shell of a module, the cartridge being used in the same manner as an assembly of cells is used in prior art modules. The term "cell" was used to refer to a prior art assembly of fibers within a frame. The term "array" was used in the '168 application in the same narrow sense as in the '535 patent, to emphasize that there was no solid support means for the fibers, other than the spaced-apart headers in which the ends of the fibers were held; in other words, the fibers in an array were unsupported between headers, as stated in the '535 patent, that is "frameless".

To position an array of fibers, one using the frameless arrays of either the '168 parent, or the '535 patent, relied upon the formation of an assembly of arrays to produce the requisite slight tension in the fibers, to keep them aligned. Such tension provides the layer-like arrangement of fibers in succeeding arrays in the assembly of arrays, each of the layers having its fibers linearly spaced apart in a plane containing both sets of the ends of fibers in a single array. A "module" was made using several post-potted cartridges which were operatively positioned in the module's shell. Because the fibers in each array would be subjected to harsh fluid flow conditions within the shell, the fibers used in our prior inventions were relatively short, in the range from 5 cm to 0.5 m (meter) long.

The problem was that the relative cost of operating a module of our prior inventions was relatively high with respect to their use in very large systems in which the cost per unit volume of permeate withdrawn was to be as low as possible. In the search to find an effective solution to the problem we improved the concept of the frameless array and built a surprisingly effective system around it.

This situation provided the impetus to cling to the arrays and abandon the module. But the main thrust of our prior inventions was to maximize the efficiency of a "module" membrane device, and to avoid the problems of directly potting the ends of fibers in individual arrays, and of cleanly severing the ends of potted fibers. We deliberately configured the arrays for assembly into a cartridge several of which were "ganged" to form a stack for use in the shell of a module. In this technical framework, it seemed as illogical to dispense with the assembly of individual arrays, as it was to dispense with the shell of the module. Yet we did both.

Because we dispensed with both requirements of our prior inventions, namely, assembling the individual arrays in a stack or cartridge, and also, using a module, in retrospect, the effectiveness and simplicity of doing so (dispensing with both), suddenly came into focus.

At first glance it was evident that giving up the benefit of both essential prerequisites for operating a module, namely, high velocity flow of "substrate" (also referred to as "multicomponent liquid feed") as well as the relatively high pressure at which it is delivered to the module, could not result in a solution to the problem. High velocity maintained the surfaces of the fibers clean, and high pressure maintained the high flux. By "multicomponent liquid feed" we refer, for example, to fruit juices to be clarified or concentrated; water containing particulate matter; proteinaceous liquid dairy products such as cheese whey, and the like. The term "particulate matter" is used to refer to micron-sized (from 1 to about 44 $\mu$m) and submicron sized (from about 0.1 to 1 $\mu$m) filtrable matter which includes not only particulate inorganic matter, but also dead and live biologically active microorganisms, colloidal dispersions, solutions of large organic molecules such as fulvic acid and humic acid, and oil emulsions.

Moreover, the problems relating to the fluid dynamic considerations relating to operating a 'moduleless' frameless array in a relatively non-turbulent substrate under atmospheric pressure, were exacerbated by the prospect of exposing the fibers to live microorganisms and small inanimate particulate material, both of which are known to be quickly deposited on all surfaces which contact any substrate containing them.

For reasons which will presently be apparent, the problems were solved by using frameless arrays buoyantly disposed in the substrate with bubbles of a fiber-cleansing gas (also referred to as a "scrubbing gas"). Each array comprises a random or ordered profusion of very long fibers, nearly always longer than 0.5 m, and often as long as 8 m or more, secured in a pair of spaced-apart "headers". The received wisdom in the art is that long fibers are highly susceptible to damage, the longer the fiber, the greater the susceptibility. This caveat derived from the observed damage in modules due to the flow of substrate being flowed over the fibers in a module at relatively high velocity.

By doing away with the conventional use of high flow at high pressure across the arrays in a module, by mounting the headers of the frameless array within a reservoir of the substrate, and by allowing the fibers free movement in the substrate, we minimized damage to the fibers. Because, a header secures a bundle of at least 10, preferably from 50 to 50,000 long fibers deployed in a loop, the bundle of fibers is also referred to as a "skein". The term "bundle" refers to a multiplicity of fibers randomly distributed in closely-spaced-apart profusion and bound by potting resin so as to present a geometrically irregular peripheral boundary around the outermost peripheries of the outermost fibers. In the skein, each fiber is free to move independently of the others. We found that the skein of fibers, freely deployed, were as ruggedly durable as they were reliable in operation.

The term "array" is used herein, as before, except that it refers to a bundle of long fibers, each fiber generally longer than 0.5 m, the opposed terminal end portions of which fibers are sealed in spaced-apart headers through both of which permeate is to be simultaneously withdrawn. Most preferably, the ends of the fibers are potted without any regard for the relative geometrical position of one fiber relative to another, so long as all fibers are substantially codirectional through one face of each header, open ends of the fibers cross the opposed other face of each header, and substantially no fibers are in fiber-to-fiber contact, thus assuring a fluid-tight seal around each fiber in the header.

In the particular instance when a porous or semipermeable membrane is in the form of a capillary tube or hollow fiber, and used for filtration, the material of the membrane divides the module into a "feed zone" and a non-feed zone referred to as a "permeate zone". The feed or substrate which is introduced either externally (referred to as "outside-in" flow) or internally ("inside-out" flow) of the fibers, is resolved into "permeate" and "concentrate" streams. The frameless array of this invention is limited for use in those instances where the flow of substrate is "outside-in" within a relatively large reservoir having a volume in excess of 10 L (liters), preferably in excess of 1000 L, such as a flowing stream, more typically a pond or tank. Most typically, plural frameless arrays with collection means for the permeate, are mounted in a tank under atmospheric pressure, and permeate is withdrawn from the tank.

In a large tank or bioreactor, where banks of frameless arrays are used, no liquid other than the permeate is removed ("dead end tank", see FIG. 5, herein). Plural frameless arrays similarly positioned adjacent one another are referred to as a "bank" of arrays. If a tank is used in conjunction with a bioreactor (for example), permeate is removed and a portion of the remaining contents (referred to as the "concentrate") of the tank is returned (see FIG. 6 herein).

The effectiveness of our system is limited to microfiltration and ultrafiltration. Operation of the system relies upon positioning spaced-apart headers of a frameless array relative to a source of sufficient cleansing gas to maintain the flux of the array, and, to enable permeate to be collected from only one, but preferably from both headers, by providing the transmembrane pressure differential of the fibers under operating process conditions. "Transmembrane pressure differential" refers to the pressure difference across a membrane wall, resulting from the process conditions under which the membrane is operating.

The relationship of flux to permeability and transmembrane pressure differential is set forth by the equation:

$$J = K\Delta P$$

wherein, $J$ = flux; $k$ = permeability constant; $\Delta P$ = transmembrane pressure differential; and $k = 1/\mu Rm$ where $\mu$ = viscosity of water and, $Rm$ = membrane resistance.

The transmembrane pressure differential may be generated either with a conventional vacuum pump, or preferably, without one, if the transmembrane pressure differential is sufficiently low in the range from 0.7 Kpa (0.1 psi) to 101 kPa (1 bar). The use of the vacuum pump may be avoided either by providing an adequate "liquid head" between the surface of the substrate and the point at which permeate is withdrawn; or, by using a pump, not a vacuum pump (referred to herein as a "non-vacuum pump"), which generates a net suction side pressure difference, or, net positive suction head (NPSH), adequate to provide the transmembrane pressure differential generated under the operating conditions. A non-vacuum pump may be a centrifugal, rotary, crossflow, flow-through, or other type. Moreover, as explained in greater detail below, once the permeate flow is induced by a pump, the pump may not be necessary, the permeate continuing to flow under a "siphoning effect". Clearly, operating with fibers subjected to a transmembrane pressure differential in the range up to 101 kPa (14.7 psi), a vacuum pump may provide adequate service if the reservoir is not pressurized; and in the range from 101 kPa to about 345 kPa (50 psi) where the reservoir is pressurized, superatmospheric pressure is generated by a liquid head; and, any combination of the foregoing, if desired.

Our system is limited to the use of a frameless array of fibers which are free and unsecured during operation, except of course, in the headers. Such unsecured fibers "sway" essentially freely in the substrate in which they are deployed, except near the headers in which the fibers are secured, the extent to which they sway being determined by the free length of the fibers relative to the spaced-apart headers, and the turbulence of the substrate.

The freely movable fibers "sway" between the headers in a curvilinear motion, and the motion of individual fibers in the skein is essentially independent of the motion of another fiber. To "sway" between spaced-apart headers, the fibers must be long enough to permit their side-to-side movement, optionally with a vertically undulating motion. Compound motion of the fibers may be the result, for example, of the substrate being agitated, or, due to convection currents in the substrate, when the fibers are long enough relative to the distance between the spaced-apart headers. When a large number of fibers in the range from 300 to 3000 or more are used in a frameless array, the movement of a fiber adjacent to others may be modulated by the movement of the others, but there is substantially no constriction of the movement of the fibers within a skein. The frameless array of this invention is therefore referred to as comprising "freely swayable" fibers, the opposed ends of which are potted in spaced-apart relationship in two spaced-apart headers, though less preferably, the opposed ends may be potted in spaced-apart relationship in only one header which provides enough space for both sets of ends.

It was accidentally observed that such freely swayable fibers not only afford excellent protection against deposits of particulate matter with the resulting maintenance of a high flux, but also afford generally better direct contact with the substrate, and, better longevity with respect to resistance to damage by impingement of the particulate matter.

The term "header" is used to specify the particular portion of material, typically a continuous mass of solid resin (plastic) of arbitrary dimensions, in which each one of the terminal end portions of a multiplicity of fibers in the skein of fibers is sealingly secured, to preclude substrate from contaminating the permeate in the lumen of the fibers. For the reason that the end portions of fibers are easily potted with individual fibers spaced-apart by cured resin, as described hereinbelow, fibers are most preferably secured by potting in a liquid, natural or synthetic resinous material, preferably thermosetting, which upon being cured, forms the header. Less preferably, any other prior art method for securing opposed terminal end portions of a bundle of fibers in proximately spaced-apart relationship with each other may be used.

When opposed terminal portions of the fibers in the skein are secured in opposed first and second headers less than about 30 cm apart in a large tank, the skein forms a loop in a generally Ω ("horse-shoe") shape. When the headers are spaced-apart by a distance greater than 30 cm the skein has a generally ∩ ("inverted U") shape, the extent to which the ∩ is "flattened" depending upon how far apart the headers are spaced. Either shape is referred to herein as being "generally parabolic".

A pair of headers with a single skein, or, a bank of plural headers with skeins, or, plural banks, one bank stacked above another, with collection means for permeate (permeate pan), are preferably removably mounted within an arbitrarily large body ("reservoir") of substrate, whether a confined substrate as in a tank or pond, or an unconfined substrate as in a flowing stream, as described in greater detail hereinbelow. The geometric relationship of one header and collection pan of the pair, relative to the other in a generally lateral plane, is not relevant, provided the skein is deployed with freely swayable fibers, that is, the fibers are free to sway with whatever movement the substrate in which they are deployed, provides. When a "bank" of frameless arrays is used, the geometric relationship of one pair of headers relative to another pair is not relevant, provided all skeins are deployed as stated.

In the specific instance where the frameless array of freely swayable fibers is used in combination with a source of cleansing gas such as air, to oxygenate the mixed liquor in a substrate, most, if not all of the air required, is introduced either continuously or intermittently, directly below the fibers in the skein. Preferably the source of the gas discharged is located relatively close to the fibers, typically less than 2 m below, so as to provide a stream of relatively large bubbles at least about 1 mm in diameter when the bubbles contact the fibers and flow over and around them. Such aeration is found to provide the physical force of impact (of bubbles on the fibers), which keeps the surfaces of the fibers sufficiently free of attached microorganisms and deposits of inanimate particles to provide a relatively high and stable flow of permeate over many weeks, if not months of operation. The significance of this improvement will be better appreciated when it is realized that the surfaces of fibers in conventional modules are cleaned every day, and usually, more often.

Because our system does away with using a shell, there is no void space within a shell to be packed with fibers; and, because of gas being introduced proximately to, and beneath a skein of fibers, there is no need to maintain a high substrate velocity across the surface of the fibers to keep the surfaces of the fibers clean. As a result, there is virtually no limit to the number of freely swayable fibers which may be used in a frameless array, the practical limit being set by (i) the ability to pot their ends reliably; and (ii) the number of arrays which may be deployed in a tank, pond or lake, the number to be determined by the size of the body of water, the rate at which permeate is to be withdrawn, and, the cost of doing so.

Typically, a relatively large number of long fibers, at least 100, each at least 0.5 meter long, are used in a frameless array of freely swayable fibers. When these fibers have a relatively low transmembrane pressure differential, the system is preferably operated with a "non-vacuum" pump to withdraw permeate. If the liquid head, measured as the vertical distance between the level of substrate and the level from which permeate is to be withdrawn, is greater than the transmembrane pressure differential of the fiber, the permeate will be separated from the remaining substrate, due to gravity, without requiring a vacuum pump. By "vacuum pump" we refer to one capable of generating a suction of at least 75 cm of Hg.

Irrespective of whether a vacuum pump or other type of pump is used, or permeate is withdrawn with a siphoning effect, it is essential that the fibers in a skein, position themselves arcuately in a generally parabolic shape, above a horizontal plane through the horizontal center-line of a header. An understanding of how the array of this invention operates will make it apparent that, since fibers in a skein are typically less dense than the substrate in which they are applied, therefore float, it is impractical to have an array of freely swayable fibers suspended below a horizontal plane through the horizontal center-line of a header.

Over the past several decades, the basic principles which govern the operation of membrane devices have become well known. How to use those principles has not; and, the concept of utilizing a frameless array of fibers, the opposed ends of which are securely held in spaced-apart headers without benefit of a shell, escaped those skilled in the art. Thus, under appropriate conditions of the system, as illustrated in FIGS. 4 to 9 herein, the frameless array with its skein of fibers in combination with a permeate collection means, is a surprisingly effective membrane device which may be operated with a low NPSH (net positive suction head) centrifugal pump even if the permeate is withdrawn from above the horizontal plane through the horizontal center-line of a header.

Since there is no module in the conventional sense, the only physical considerations which affect the operation of a frameless array in a reservoir of substrate, are the intrinsic considerations relating to the hollow fiber membrane, and to the substrate. Such considerations include the permeability and rejection properties of the fiber, the process flow conditions of substrate such as pressure, rate of flow across the fibers, temperature, etc., the physical and chemical properties of the substrate and its components, the relative directions of flow of the substrate (if it is flowing) and permeate, the thoroughness of contact of the substrate with the walls of the fibers, and still other parameters, each of which has a direct effect on the efficiency of the array. The goal is to maximize the efficiency of an array and to do so, practically and economically.

It is now readily apparent that when the skein of a frameless array is freely deployed as described herein, any problem relating to channelling of the feed due to uneven distribution of the fibers, is essentially negated because the fibers stay suspended in, and floatingly sway in the substrate to be filtered. Further, since the fibers are evenly contacted over their individual surfaces as they sway in the substrate, the array provides filtration performance based on maximized surface area of fibers. This performance is based on substantially the sum of the surface area of each fiber in the skein. Moreover, because of the ease with which the substrate coats the surfaces of the fibers, they may be arranged as a dense bundle in a single header portion making it economical to deploy an array of large membrane surface up to 1000 m$^2$ and more.

The fibers used in the arrays of this invention are not required to have a narrowly critical transmembrane pressure differential though fibers with low transmembrane pressure differential are preferred. A fiber which operates under a small transmembrane pressure differential in the range from about 0.7 kPa (0.1 psi) to about 206 kPa (30 psi), preferably, 3.5 kPa (0.5 psi) to about 70 Kpa (10 psi) may produce permeate under gravity alone, if appropriately positioned relative to the location where the permeate is withdrawn; the longer the fiber, the more the permeate.

Routinely, hollow fibers are potted near opposed ends in opposed headers which are adapted to be inserted, using suitable gasketing means, in fluid-tight engagement with the interior wall of the casing of a conventional module. The membrane area which one can provide in such a module is limited to the size of the header and the packing density of the fibers in the module. Since packing density is not a limitation in the frameless array of this invention, and there is no module, it is now readily apparent that the use of the frameless array will be more economical than a module which delivers the same flow of permeate.

This invention allows one to position a large number of fibers, randomly relative to one another, within each header of organic synthetic resinous material. There is no reason to position the fibers precisely before they are potted, thus avoiding the numerous pitfalls in "potting" the terminal portions of fibers in a resin which can be solidified. When potted, and the header cut (sectioned) with a sharp blade to expose the open ends of the fibers, the end surface of each header appears to be foraminous due to the open ends of the fibers. The solid resin forms a seal around the exterior terminal portions of each of the fibers planarly disposed in the sectioned plane of the header.

Further, one does not have to cope with the geometry of a frame which is to support each arrangement of fibers, because in a frameless array, there is no frame.

The frameless array of this invention is most preferably used to treat wastewater in combination with a source of an oxygen-containing gas which is bubbled within the substrate, below and within, preferably directly beneath the arch of fibers deployed in the substrate, for the specific purpose of oxygenating the mixed liquor in activated sludge, such as is used in the bioremediation of wastewater. It was found that, as long as enough air is introduced directly beneath the upper portion of the skein, or near the base of each spaced-apart header to keep the fibers awash in bubbles, and the fibers are buoyantly freely swayable in the activated sludge so as to present an arcuate profile (when viewed in a side elevational view) above the plane in which the header portions lie, a buildup of growth of microbes on the surfaces of the fibers is inhibited while permeate is directly withdrawn from activated sludge, and excellent flow of permeate is maintained over a long period. Because essentially all surface portions of the fibers intercept successive bubbles as they rise, whether the air is supplied continuously or intermittently, the fibers are said to be "awash in bubbles."

The use of an array of fibers in the direct treatment of activated sludge in a bioreactor, is described in an article titled "Direct Solid-Liquid Separation Using Hollow Fiber Membrane in an Activated Sludge Aeration Tank" by Kazuo Yamamoto et al. in Wat. Sci. Tech. Vol. 21, Brighton pp 43-54, 1989. They state "Three hollow fiber membrane units (Mitsubishi Rayon Engineering Co., Ltd.) (note that each unit is shown having 3 fibers in the illustrations, FIGS. 1 and 2) were immersed and suspended vertically in the reactor. The membranes were made of polyethylene with pore size of 0.1 micron, which falls in microfiltration range."

Since polyethylene fibers float, presumably the fibers were tied to a rod so as to be suspended vertically downward in the reactor. They state "Air was supplied with at the bottom of the reactor with an air flow rate of 1.8 L/min." (see lines 8-9 from bottom of pg 44). The ends of the fibers in each unit are shown to be secured in a single header to which a vacuum is applied, either continuously or intermittently, to withdraw permeate from the downwardly suspended membranes. There is no indication as to what the source of air was, or the means used to introduce the air into the reactor. Nor is there any purpose stated for introducing the air other than to maintain the microorganisms.

The downwardly suspended configuration of the fibers resulted in clogging to some extent, immediately after the start of filtration and the flux became insensitive to the pressure difference with elapse of time. (see bottom of pg 46). In another run, changes in the flux and pressure difference with time, indicate that "the initial flux was $2.5 \times 10^{-6}$ m$^3$/(m$^2$.sec) 90 liters/m$^2$.hr) and the pressure difference increased to 100 kPa, reached under vacuum, and the flux decreased sharply in 5 days after starting the run. It was observed that the severe clogging had occurred in the first 5 days. It seemed as if the module were a stick of sludge. . . . Back washing using the effluent or air was tried several times, but it was not successful. Though a little recovery was obtained after back washing, yet the flux was immediately returned to the previous one." (see sentences bridging pgs 47-48).

Yamamoto et al. stated that "clogging may proceed at low mixed liquor suspended solids (MLSS) concentrations applying high pressure difference. It leads to the conclusion that continuous suction cannot be applied for long-term stable operation. Once clogging occurs in the membrane module, it increases the pressure difference and the increase in pressure difference, in turn, promotes clogging, which ultimately results in an unrecoverable dead end operation." (see pg 48, second full paragraph).

The relatively poor performance obtained by Yamamoto et al. was mainly due to the fact that they did not realize the critical importance of maintaining flux by aerating a skein of fibers from within and beneath the skein. In other words, they did not realize the necessity of thoroughly scrubbing substantially the entire surfaces of the fibers by flowing bubbles through the skein to keep the fibers awash in bubbles. This requirement becomes more pronounced as the number of fibers in the skein increases. Because Yamamoto et al. suspended the fibers downward in their test reactor, they were unable to aerate their skein of three fibers from beneath the arch they would have formed, had the fibers been inverted in the substrate.

Further, it has now been discovered that the very small bubbles in the range from about 10 μm but smaller than 1 mm in diameter are ineffective to prevent the build-up of growth of microorganisms on the fibers. It appears that the force associated with such small bubbles is insufficient either to deny the microorganisms an adequate initial hold or 'grip' onto the surface of the fibers, or to dislodge them if they have succeeded in establishing such a hold.

As will presently be evident, since most substrates are contaminated with micron and submicron size particulate material, both organic and inorganic, the surfaces of the fibers in any practical membrane device must be maintained in a clean condition. To do this, the most preferred use of the frameless array as a membrane device is as an assembly, in combination with a gas-distribution means, which is typically used to distribute a fiber-cleansing gas such as air, or oxygen-enriched air through the fibers, from within the skein and directly under the fibers.

Tests using the device of Yamamoto et al. indicate that when the air is provided outside the skein the flux decreases much faster over a period of as little as 50 hr, confirming the results obtained by them. This is evident in FIG. 1 herein, in which the results obtained by Yamamoto et al. are compared with the device of this invention, both devices using essentially identical fibers aerated with the same amount of air, under essentially identical conditions as those used by Yamamoto et al. The only difference in each test is that the air, for our device, was distributed beneath and within the arch provided by the skein of freely swayable fibers.

The investigation of Yamamoto et al. with downwardly suspended fibers was continued and recent developments were reported in an article titled "Organic Stabilization and Nitrogen Removal in Membrane Separation Bioreactor for Domestic Wastewater Treatment" by C. Chiemchaisri et al. delivered in a talk to the Conference on Membrane Technology in Wastewater Management, in Cape Town, South Africa, Mar. 2–5, 1992. An improvement in flux was sought by providing a highly turbulent condition within a separation zone in cooperation with jet aeration installed inside the membrane module but outside the suspended fibers. The separation zone appears to be in open flow communication with the contents of the bioreactor. The module included a main bioreactor and a separation unit immersed in the bioreactor.

Two hollow fiber membranes, each having a surface area of 0.3 m$^2$ and supported on a frame, were suspended inside the separation unit so that the fibers hung on either side of a paddle stirrer, beneath a header in which the fibers were potted. Permeate was extracted with a suction pump under intermittent operating conditions, and the paddle stirrer, driven by a motor, provided cross flow of mixed liquor across the membrane surface. The direction of rotation of the paddles which rotated at 290 rpm, was changed every 10 secs. In addition jet aeration was provided once in 90 min for a duration of 1 min; the direction of the air jet being radial relative to the fibers, so that the air was blown across the suspended fibers. The combination of the above conditions provided a high flux because growth of the microbes was inhibited.

In the foregoing Chiemchaisri disclosure it is evident that the fibers are suspended downwardly and that highly turbulent flow of water in alternate directions, is essential. This configuration does not permit permeate to be withdrawn under gravity alone, without the use of a suction pump. Finally, from an economic point of view, the high costs of operating a bioreactor as described in the Chiemchaisri et al. article are no more favorable than operating a similar bioreactor in combination with an exteriorly disposed semipermeable membrane module.

It is evident that the disclosure in either the Yamamoto et al. or the Chiemchaisri et al. reference indicated that the flow of air across the surfaces of the suspended fibers did nothing to inhibit the attachment of microorganisms from the substrate.

SUMMARY OF THE INVENTION

It has been discovered that the build-up of growing microbes, or, the deposits of inanimate particles, upon the surfaces of fibers kept awash in bubbles of a fiber-cleansing gas ("scrubbing gas"), particularly an oxygen-containing gas ("air-scrubbed"), is essentially negated when the fibers are buoyantly freely swayable in a frameless array submerged in a substrate through which the bubbles rise with sufficient physical force of impact (momentum and energy) to keep the fibers essentially free of deleterious deposits; thus an unexpectedly high flux is maintained over a long period during which permeate is produced by outside-in flow through the fibers.

It has also been discovered that by mounting a pair of headers in spaced-apart relationship within a substrate in direct contact with a multiplicity of long fibers in a gas-scrubbed assembly comprising a frameless array and a gas-distribution means, permeate may be withdrawn from the substrate for a surprisingly long period, with effectiveness and efficiency. The frameless array has a surface area which is at least >1 m$^2$, and opposed ends of the fibers are secured in spaced-apart but proximately disposed headers, so that the fibers, when deployed, acquire a generally parabolic profile within the substrate and sway freely therein. The array is part of a membrane device which operates without being confined within the shell of a module, in a substrate held in a reservoir at a pressure in the range from 1 atm to an elevated pressure up to about 10 atm. The fibers are longer than the distance separating the headers in which the terminal end portions of the fibers are potted, so that the fibers arch above a line connecting the headers. The terminal end portions of the fibers are secured non-contiguously in each header, that is, the surface of each fiber is sealingly separated from that of another adjacent fiber with cured potting resin. Unless deliberately set in a geometrically regular pattern, the open ends of the fibers are randomly distributed relative to one another within the permeate-discharging (usually lower) face of a header through which permeate is withdrawn. The overall geometry of potted fibers will be determined by the 'fiber-setting form', if such is used to set individual fibers, but in general, individual fibers along the periphery of the form are also irregularly spaced relative to one another.

It is therefore a general object of this invention to provide a novel, economical and surprisingly trouble-free membrane device comprising, a frameless array of a multiplicity of buoyantly, freely swayable hollow fiber membranes, together having a surface area preferably in the range from 1 m$^2$ to 1000 m$^2$, preferably from 10 m$^2$ to 100 m$^2$, unsupported other than by the substrate, and secured only in spaced-apart headers. For operation, the membrane device is combined with permeate pans disposed, preferably removably, within a reservoir of arbitrary proportions containing substrate, the reservoir typically having a volume in excess of 100 L (liters), generally in excess of 1000 L. A fluid component is to be selectively removed from the substrate. A collection means is provided to collect and remove the fluid component as a permeate.

It is a specific object of this invention to provide a membrane device having hollow fibers for removing permeate from a substrate, comprising, a frameless array of a multiplicity of hollow fiber membranes or fibers buoyantly freely swayable as a skein in the substrate, the opposed terminal end portions of which fibers in spaced-apart relationship, are potted in a pair of first and second headers adapted to be mounted within the substrate and beneath the swayable fibers, essentially all the ends of fibers in both headers being open so as to discharge permeate through both headers, the fibers having a length sufficiently greater than the direct distance between said first and second headers, so as to present, when said fibers are deployed, an arcuate, generally parabolic fiber configuration; collection means, such as a permeate pan, to collect the permeate; and, ducting means to withdraw the permeate.

It has also been discovered that when a skein of fibers between spaced-apart headers of a frameless array is immersed in a substrate so as to present a generally parabolic profile above the horizontal plane through the horizontal center-line of a header, and, the skein is maintained awash with bubbles continuously or intermittently generated by a gas-distribution means which is preferably proximately disposed relative to the fibers within a zone therebeneath, the fibers are maintained essentially free from particulate deposits in an amount sufficient to vitiate the flux at equilibrium, deleteriously. The bubbles are generated directly beneath the skein and within the arcuate form provided by the skein above the gas-distribution means, preferably spaced in the range from 1 cm to about 50 cm from the fibers nearest and farthest, respectively, from the gas-distribution means, so as to maintain essentially the entire length of each fiber in the skein awash with bubbles. The skein is referred to as being "gas-scrubbed" directly above the gas-distribution means which is preferably disposed between rows of fibers in each header, or between the headers, and beneath the generally parabolic configuration of the skein.

It is therefore a general object of this invention to provide a fiber-cleansing or gas-scrubbing assembly which separates a desired permeate from a large body of multi-component substrate having finely divided particulate matter in the range from 0.1 $\mu$m–44 $\mu$m dispersed therein, by filtration, the fiber-cleansing assembly comprising, (a) a frameless array of potted fibers comprising spaced-apart first and second headers, each having first and second opposed terminal end portions respectively, of at least 20 fibers essentially freely swayable in a skein between the headers, in a generally parabolic configuration, and (b) a shaped gas-distribution means adapted to provide a profusion of bubbles beneath the fibers, the length of the fibers being greater than the center-to-center distance between the headers. The gas-distribution means has through-passages therein which, when gas is flowed through them at a flow rate in the range from 0.3 $m^3$/day/$m^2$ to 400 $m^3$/day/$m^2$ ($meter^3$ per day per $meter^2$ of fiber surface area), generate bubbles having an average diameter in the range from about 1 mm to about 50 mm, or even larger, preferably discharged in relatively close proximity, both to a lower zone near the base of the skein, and to an upper zone containing the remainder of the skein, so as to maintain each fiber in the skein awash with bubbles and improve resistance of the pores of the fibers to being clogged by deposits deposited from the substrate.

It is a specific object of this invention to provide the aforesaid gas-scrubbing assembly comprising, a novel membrane device and a gas-distribution means for use in a tank of substrate in which microorganisms grow in the substrate, the assembly being used in combination with means for mounting the headers in open fluid communication with collection means for collecting the permeate; means for withdrawing the permeate; and, sufficient air is flowed through the shaped gas-distribution means to generate enough bubbles flowing upwardly through the skein around and between the fibers to keep the surfaces of the fibers essentially free from deposits of live microorganisms as well as small inanimate particles which may be present in the substrate; whereby the gas-scrubbing assembly avoids the problems of using a module, as used in the prior art, instead of overcoming them.

It has still further been discovered that a system utilizing spaced-apart headers and an unsupported skein of fibers deployed in a substrate containing particulate material, in a generally parabolic configuration, preferably in combination with a proximately disposed gas-distribution means to minimize fouling of the membranes, may be operated to withdraw permeate under gravity alone, so that the cost of any pump to withdraw permeate is avoided, provided the net positive suction head corresponding to the vertical height between the level of substrate, and the location of withdrawal of permeate, provides the transmembrane pressure differential of the fibers in the skein.

It is therefore a general object of this invention to provide a system for removing permeate from a substrate in which a gas, particularly an oxygen-containing gas, typically air, is introduced to maintain the growth of microorganisms, the system comprising, an arbitrarily large body of a substrate, a frameless array of fibers each > 0.5 m long, opposed ends of which are essentially free from fiber-to-fiber contact after being potted in spaced-apart headers deployed in the substrate without being supported during operation except by the substrate, and without being confined in a shell of a module, at least one header mounted so that the fibers present a generally parabolic profile above a horizontal plane through the horizontal center-line of the one header; in combination with, means for mounting the spaced-apart headers in open fluid communication with collection means for collecting the permeate, and, means for withdrawing the permeate; and, a shaped gas-distribution means adapted to generate bubbles, most preferably in the size range from 1 mm to 25 mm, at a flow rate in the range from 3 $m^3$/day/$m^2$ to 30 $m^3$/day/$m^2$ which flow upwardly through fibers of the array, whereby the fibers are scrubbed with bubbles and resist the attachment of growing microorganisms and any other particulate matter thereto.

Still further, a low cost process has been discovered for treating a multicomponent substrate under pressure ranging from 1–10 atm, particularly for example, an aqueous stream containing finely divided inorganic matter such as silica, silicic acid, or, activated sludge, when the substrate is confined in a large tank or pond, by using an assembly of a frameless array with a skein of freely swayable unsupported fibers in open fluid communication with a means for withdrawing permeate, in combination with a source of air which generates bubbles beneath the fibers, preferably directly thereneath, and in relatively close proximity thereto.

It is therefore a general object of this invention to provide a process for maintaining relatively clean fiber surfaces in an array of a membrane device while separating a permeate from a substrate, the process comprising, submerging a frameless array of buoyantly freely swayable fibers within the substrate so that first and second headers of the frameless array are mounted below an unsupported skein of a multiplicity of fibers secured in the first and second headers; the fibers providing a transmembrane pressure differential in the range from about 0.7 kPa (0.1 psi) to about 345 kPa (50 psi), and a length sufficiently greater than the direct distance between the first and second headers, so as to present, when the fibers are deployed, a generally parabolic fiber configuration above a horizontal plane through the horizontal center-line of a header; maintaining an essentially constant flux substantially the same as the equilibrium flux initially obtained, indicating that the surfaces of the fibers are essentially free from further build-up of deposits once the equilibrium flux is attained; collecting the permeate by mounting the headers in open fluid communication with means to collect the permeate; and, withdrawing the permeate.

It has still further been discovered that the foregoing process may be used in the operation of an aerobic biological reactor which has been retrofitted with the membrane device of this invention.

It is therefore a general object of this invention to provide an aerobic biological reactor retrofitted with at least one membrane device comprising an array in combination with a permeate collection means, preferably plural membrane devices, from 2 to 100, in a bank, or plural banks of membrane devices, and, a process for the reactor's operation without being encumbered by the numerous restrictions and limitations imposed by a secondary clarification system.

BRIEF DESCRIPTION OF THE DRAWINGS

The foregoing and additional objects and advantages of the invention will best be understood by reference to the following detailed description, accompanied by schematic illustrations of preferred embodiments of the invention, in which illustrations like reference numerals refer to like elements, and in which.

DETAILED DESCRIPTION OF PREFERRED EMBODIMENTS

Figure 1:
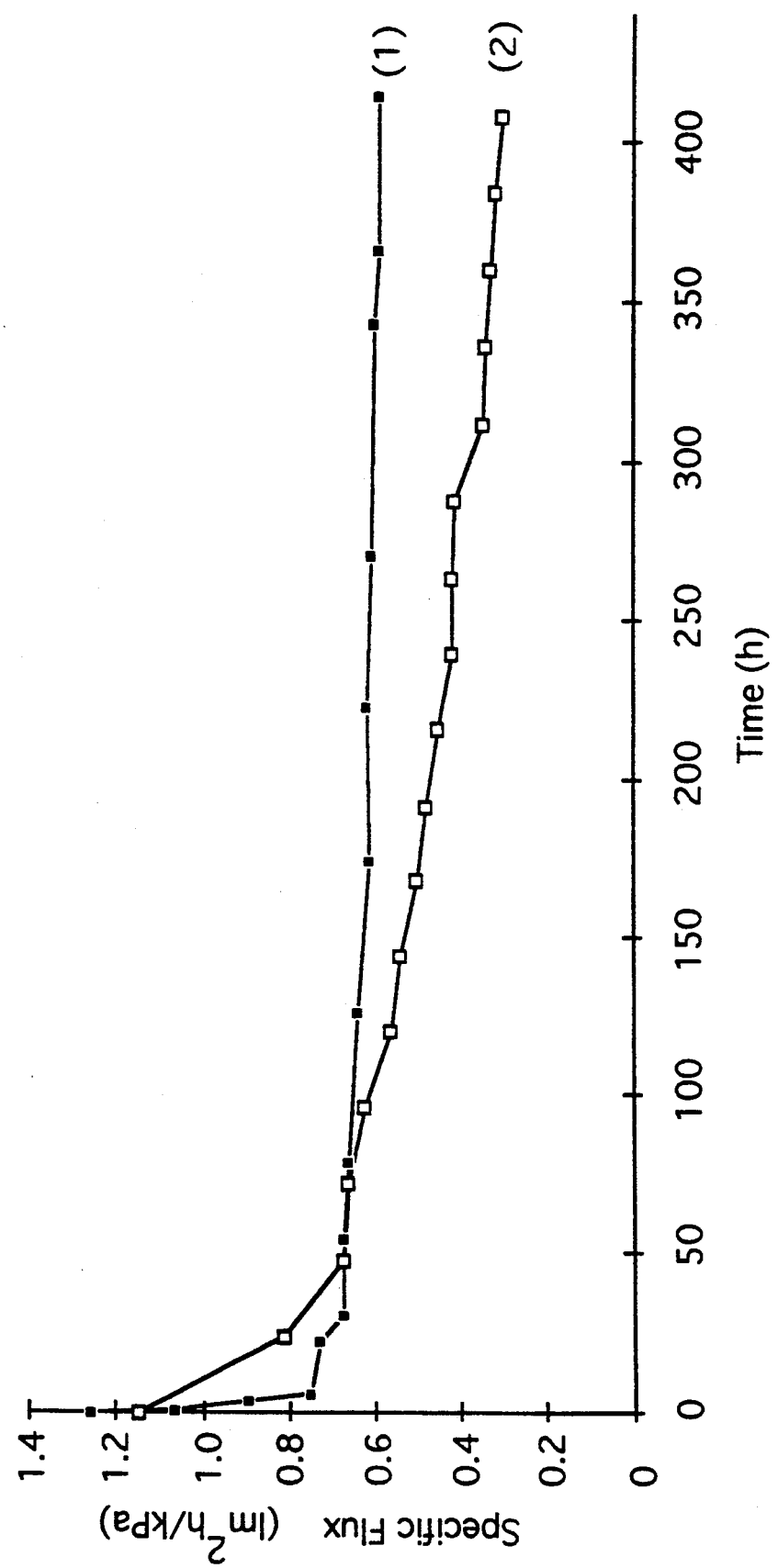
FIG. 1 is a graph in which the variation of flux is plotted as a function of time, comparing the results obtained by Yamamoto et al. (under conditions modified to give them the benefit of doubt as to the experimental procedure employed, as explained below) with those obtained using the membrane device of this invention, each using the same amount of air, and the same membrane surface area.

The frameless array of this invention may be used in a liquid-liquid separation process of choice, and more generally, in various separation processes. The array is specifically adapted for use in microfiltration and ultrafiltration processes used to remove large organic molecules, emulsified organic liquids and colloidal or suspended solids, usually from water. Typical applications are (i) in a membrane bioreactor, to produce permeate as purified water and recycle biomass; for (ii) tertiary filtration of wastewater to remove suspended solids and pathogenic bacteria and viruses; (iii) clarification of aqueous streams including filtration of surface water to produce drinking water (removal of colloids, long chain carboxylic acids and pathogens); (iv) separation of a permeable liquid component in biotechnology broths; (v) dewatering of metal hydroxide sludges; and, (vi) filtration of oily wastewater, inter alia.

The problem of using a membrane module to selectively separate one fluid from another, particularly using a module in combination with a bioreactor, and the attendant costs of operating such a system, have been avoided. In those instances where an underdeveloped country or distressed community lacks the resources to provide membrane modules, the most preferred embodiment of this invention is adapted for use without any pumps. In those instances where a pump is conveniently used, a vacuum pump is unnecessary, adequate driving force being provided by a simple centrifugal pump incapable of inducing a vacuum of 75 cm Hg on the suction side.

The fibers used to form the skein of an array may be formed of any conventional membrane material provided the fibers are flexible. Preferred fibers operate with a transmembrane pressure differential in the range from about 3.5 kPa (0.5 psi) to about 175 kPa (25 psi). Most preferred are fibers which provide a transmembrane pressure differential in the range from 7 kPa (1 psi)–69 Kpa (10 psi).

Preferred fibers are made of organic polymers and ceramics, whether isotropic, or anisotropic, with a thin layer or "skin" on the outside surface of the fibers. Some fibers may be made from braided cotton covered with a porous natural rubber latex or a water-insoluble cellulosic polymeric material. Preferred organic polymers for fibers are polysulfones, poly(styrenes), including styrene-containing copolymers such as acrylonitrile-styrene, butadiene-styrene and styrene-vinylbenzylhalide copolymers, polycarbonates, cellulosic polymers, polypropylene, poly(vinyl chloride), poly(ethylene terephthalate), and the like disclosed in U.S. Pat. No. 4,230,463 the disclosure of which is incorporated by reference thereto as if fully set forth herein. Preferred ceramic fibers are made from alumina, by E. I. duPont deNemours Co. and disclosed in U.S. Pat. No. 4,069,157.

The fibers are chosen with a view to perform their desired function, and are deployed in the substrate to form an unsupported arch or loop, the dimensions of the arch or loop being determined by the length of the skein and the spacing of the headers. Though, the generally parabolic arch formed is usually symmetrical because the headers are coplanarly disposed within the substrate, the shape of the arch may also be asymmetrical. The arch is asymmetrical when one header is disposed at a lower level, transversely spaced-apart from the other. In no case is an array confined in a modular shell.

Typically, there is no cross flow of substrate across the surface of the fibers in a "dead end" tank. If there is any flow of substrate through the skein in a dead end tank, the flow is due to aeration provided beneath the skein, or to such mechanical mixing as may be employed to maintain the solids in suspension. There is more flow through the skein in a tank into which substrate is being continuously flowed, but the velocity of fluid across the fibers is generally too insignificant to deter growing microorganisms from attaching themselves, or suspended particles, e.g. microscopic siliceous particles, from being deposited on the surfaces of the fibers.

For hollow fiber membranes, the outside diameter of a fiber is at least 20 $\mu$m and may be as large as about 3 mm, typically being in the range from about 0.1 mm to 2 mm. The larger the outside diameter the less desirable the ratio of surface area per unit volume of fiber. The wall thickness of a fiber is at least 5 $\mu$m and may be as much as 1.2 mm, typically being in the range from about 15% to about 60% of the outside diameter of the fiber, most preferably from 0.5 mm to 1.2 mm.

The average pore cross sectional diameter in a fiber may vary widely, being in the range from about 5 to 10000Å. The preferred pore diameter for ultrafiltration of components in a substrate feedstream being in the range from about 5Å to 1000Å; and for microfiltration, in the range from 1000Å to 10000Å.

Unlike in a conventional module, the length of a fiber in a skein is essentially independent of the strength of the fiber, or its diameter, because the skein is buoyed, both by bubbles and the substrate in which it is deployed. The length of each fiber in the skein is preferably determined by the conditions under which the array is to operate. Typically fibers range from 1 m to about 5 m long, depending upon the dimensions of the body of substrate (depth and width) in which the array is deployed.

The materials for the headers are most preferably either thermosetting or thermoplastic synthetic resinous materials, optionally reinforced with glass fibers, boron or graphite fibers and the like. Thermoplastic materials are preferred for relatively low temperature service below 100° C., these being chosen so as to be sufficiently compatible with the material of the fibers to produce a lasting, fluid-tight bond. Such thermoplastic materials may be crystalline, such as polyolefins, polyamides (nylon), polycarbonates and the like, semi-crystalline such as polyetherether ketone (PEEK), or substantially amorphous, such as poly(vinyl chloride) (PVC) and the like. Thermosetting resins are preferred for higher temperature service, and for ease of use.

The number of fibers in an array is arbitrary, typically being in the range from about 1000 to about 10000, and the preferred surface area for a skein is in the range from 10 m² to 100 m².

The particular method of securing the fibers in each of the headers is not narrowly critical, the choice depending upon the materials of the header and the fiber, and the cost of using a method other than potting. However, it is essential that each of the fibers be secured in fluid-tight relationship within each header. This may be effected by simply not bundling the terminal portions of the fibers too tightly before potting them.

FIG. 1 presents the results of a comparison of two runs made, one using the teachings of Yamamoto in his '89 publication (curve 2), but using an aerator which introduced air from the side and directed it radially inwards, as is shown in Chiemchaisri et al. The other run uses the process and frameless array of this invention (curve 1). The only differences in the runs are detailed in Example 3 herebelow.

As can be seen, the flux, liters/meter²-hr/kPa (conventionally written as (1 mh/kPa), obtained with the frameless array reaches an equilibrium condition within less than 50 hr, while the flux for the Yamamoto replication continues to decline. It will be evident that the results obtained with the Yamamoto replication are much better than the ones he reported, and those with the frameless array are better still. Further details of the comparison are provided in the illustrative examples.

Figure 2:
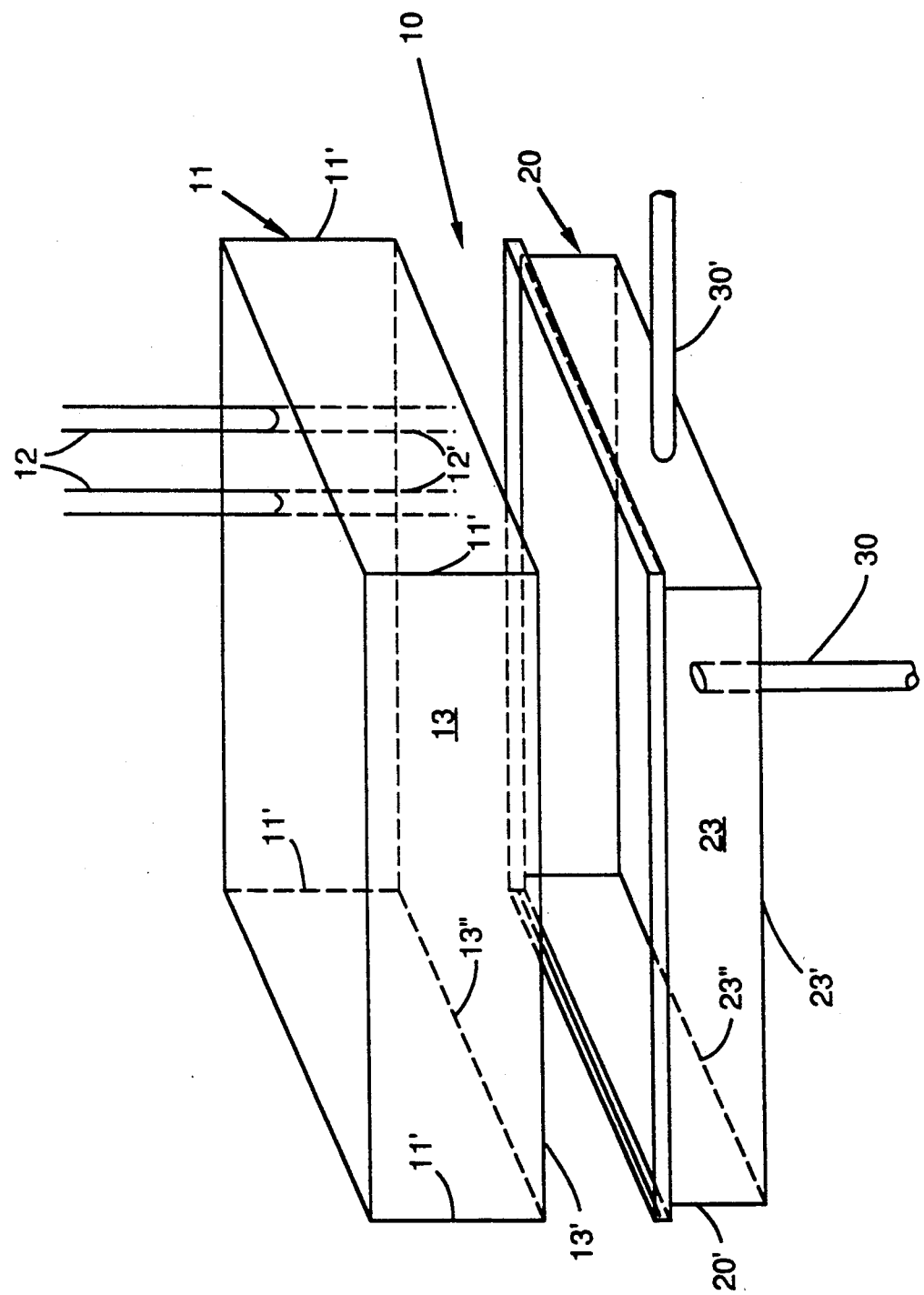
FIG. 2 is a perspective exploded view schematically illustrating a membrane device comprising a frameless array of a skein of fibers, unsupported during operation of the device, with the ends of the fibers potted in spaced apart headers, along with a permeate collection pan, and a permeate withdrawal conduit. By "unsupported" is meant 'not supported during operation of the membrane device, except by the substrate'.

Referring to FIG. 2 there is illustrated, in exploded view a membrane device referred to generally by reference numeral 10, comprising one header 11 of a pair of headers, the other being substantially identical; a collection pan 20 to collect the permeate, and a permeate withdrawal conduit 30. The header shown is rectangular since this is the most convenient shape to make, if one is going to pot fibers 12 in a potting resin such as an epoxy. Though the fibers 12 are not shown as close toothier as they would normally be, it is clear that the fibers are not in contact with each other but spaced apart by the cured epoxy between them.

To form the header 11, any conventional method may be used, and forms no part of this invention, but an illustration of how a header is typically formed, follows:

A bundle of fibers is held in the spaced-apart arms of a fixture. The arms, at their ends, have circular clamping means, for example an adjustable (with a screw) hose clamp, lined with rubber tape, which snugly holds each side of the bundle together so that the bundle hangs in a parabolic loop below the arms. At the midpoint between the arms and below them, near the apex of the parabolic loop, the fibers are closely spaced-apart. A rectangular potting pan containing uncured liquid potting resin is then placed under the bundle so that all fibers in the loop are submerged sufficiently to ensure that, when the resin cures, the fibers will be securely potted. The resin covers each fiber to a depth of about 1 cm to 5 cm, preferably 2-5 cm, on either side of the axis of the loop. When the resin cures, the fibers are potted in the cured block. The block is then sectioned in a vertical plane through the axis of the loop, exposing open ends of the fibers.

The block has front and rear walls defined by vertical (z-axis) edges 11' and lateral (x-axis) edges 13'; side walls defined by edges 11' and transverse (y-axis) edges 13"; and a base 13 defined by edges 13' and 13". The bottom of the block is then cut off in the horizontal plane with a sharp blade exposing the open ends of the fibers.

The collection pan 20 is sized to snugly accommodate the base 13 above a permeate collection zone within the pan. This is conveniently done by forming a rectangular pan having a base 23 of substantially the same length and width dimensions as the base 13. The periphery of the pan 20 is provided with a peripheral channel as shown in FIG. 2A, in which the wall 20' of the pan terminates in a channel section 22, having a substantially horizontal shoulder 22" and a vertical retaining wall 22'.

Figure 2B:
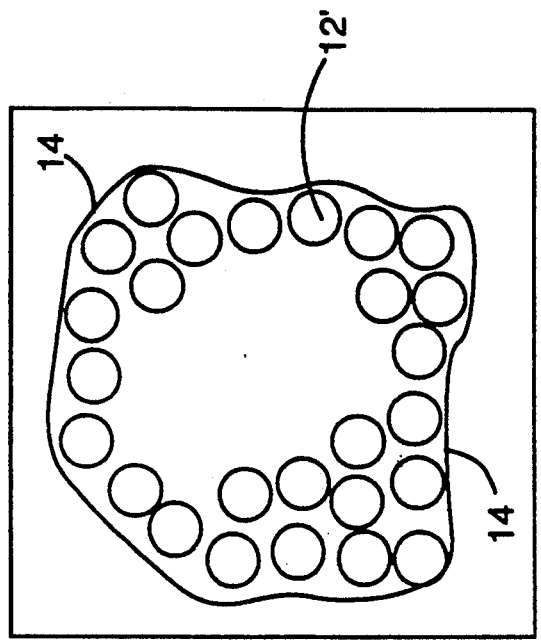
FIG. 2B is a bottom plan view of the header showing the random spaced-apart distribution of the open ends of the fibers in the lower face of the header.
Figure 2A:
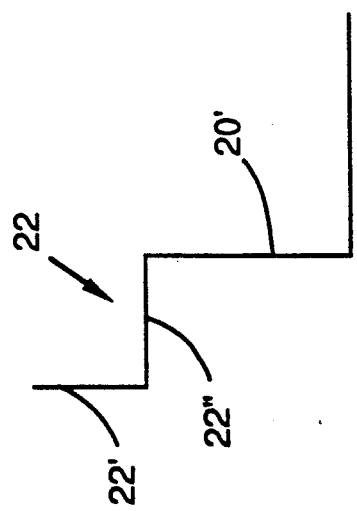
FIG. 2A is an enlarged detail side elevational view of a side wall of a collection pan showing the profile of a channel atop the periphery of the pan.

FIG. 2B is a bottom plan view of the lower face of header 13 showing the open ends of the fibers 12' prevented from touching each other by potting resin. The random distribution of fibers is uniquely distinguished by the geometrically irregular peripheral boundary 14 (shown in dotted outline) which bounds the outermost peripheries of randomly distributed outermost open ends 12'.

Permeate flows from the open ends of the fibers onto the base 23 of the pan 20, and flows out of the collection zone through a permeate withdrawal conduit 30 which may be placed in the bottom of the pan in open flow communication with the inner portion of the pan. If desired, the withdrawal conduit may be positioned in the side of the pan as illustrated by conduit 30'. Whether operating under transmembrane pressure differential provided by gravity alone, or by a pump, it will be apparent that a fluid-tight seal is necessary between the periphery of the header 11 and the peripheral channel 22 of the pan 20. Such a seal is obtained by using any conventional means such as a suitable sealing gasket or sealing compound, typically a silicone resin, between the lower periphery of the header 11 and the channel 22.

It will now be evident that a header with a circular periphery may be constructed, if desired. Headers with geometries having still other peripheries (for example, an ellipse) may be constructed in an analogous manner, if desired, but rectangular headers are most preferred.

Individual fibers 12 (FIG. 2) extend generally parallel to one another near each header and end portions of the fibers extend through the headers so that the fibers' open ends 12' are exposed at the lower face 13 of the header. In a skein, the center-to-center spacing of fibers in the horizontal plane ranges from about 1.2 to about 5 times the outside diameter of a fiber. The choice of fiber spacing in the header will determine packing density of the fibers near the headers, but is not a substantial consideration with respect to the relative positions between individual fibers in a skein, though it will be evident, the more fibers, more tightly packed together in each header, the less space between fibers in the skein.

The density of fibers in a header is chosen to provide the maximum membrane area per unit volume of substrate without adversely affecting the circulation of substrate through the skein. Instead of mounting the headers in a collection pan with a downward discharge relative to the buoyantly suspended skein, as described, it will now be evident, that the headers with pans may also be mounted so that the permeate is discharged laterally in opposite directions, or even in the same lateral direction, and the skein could still be deployed with a parabolic profile, if the fibers are long enough. However, it will be seen that in each case the location for withdrawal of the permeate is below the fibers, and that the most convenient way of mounting the headers results in permeate being discharged downwards.

Though a skein deployed in a substrate presents a generally parabolic profile, it has no structural shape, and such shape as it does have changes continuously, the degree of change depending upon the flexibility of the fibers, their lengths, the overall dimensions of the shape of the skein, and the degree of movement imparted to the fibers by the substrate and by the oxygen-containing gas from the gas-distribution means, if such is used. Neither does the skein have a structural shape before the headers with their respective permeate pans are mounted, in that each of the two headers with pans are displaceable in any direction relative to the other, the displacement being limited only by their attachment to the fibers.

Figure 3:
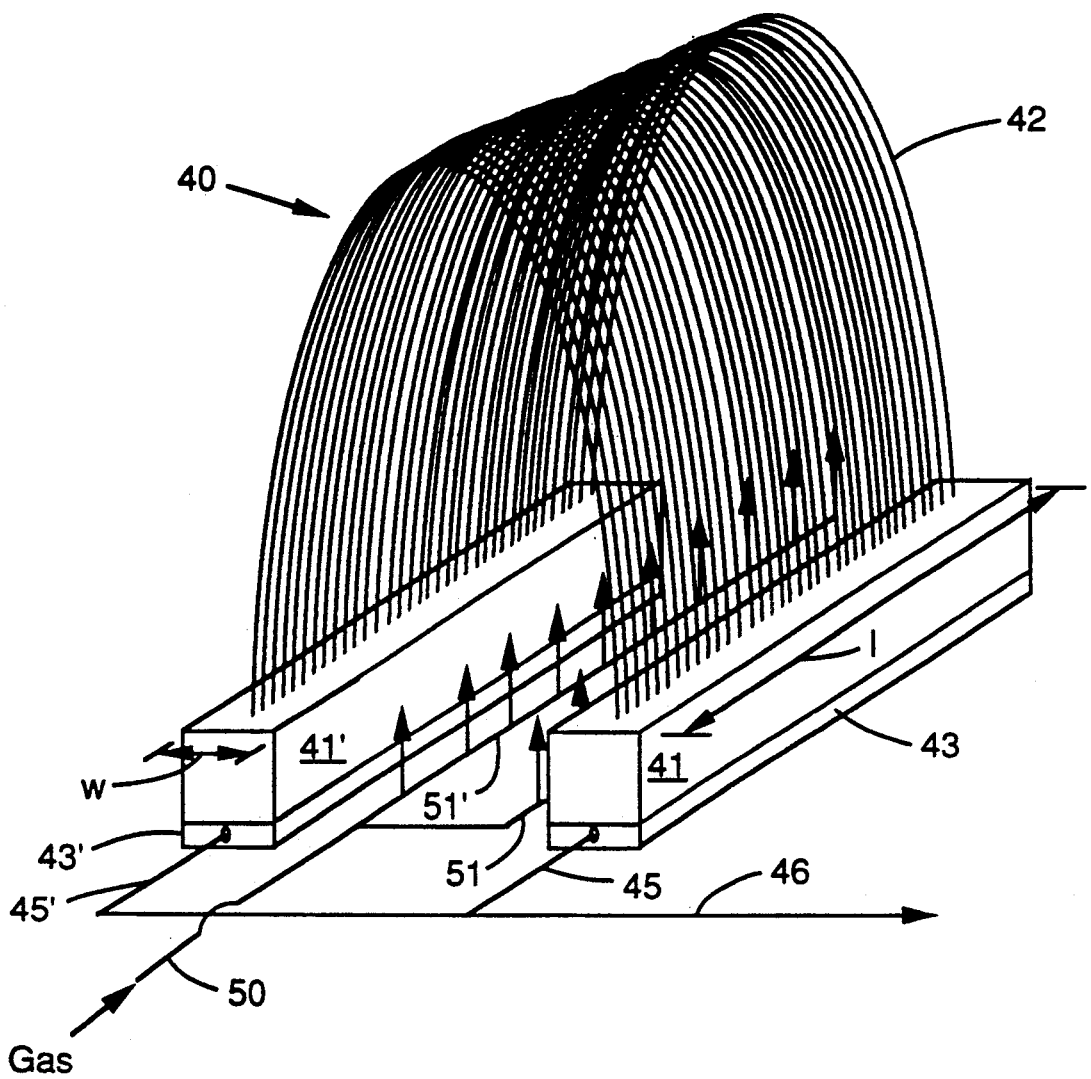
FIG. 3 is a perspective view of a combination of a membrane device (assembly of a frameless array with permeate pan), and, a gas-distribution means, as the combination "scrubbing assembly" would appear when deployed within a substrate, showing the parabolic arch of fibers buoyantly suspended in the substrate, and the gas-distribution means disposed between the headers and directly beneath the arched fibers, so that the bubbles are generated within the zone under the fibers.

Referring to FIG. 3 there is illustrated a typical assembly, indicated generally by reference numeral 40, for use in a tank, the assembly comprising a bundle of fibers 42 and a gas-distribution means 50. The bundle (only one row of which is shown in this view for obvious reasons) shown in this end view, is an elongated rectangular shape with irregular sides because of the random displacement of fibers along each side. The rectangular shape may be relatively square or quite narrow, depending upon the ratio of the number of fibers in each transverse row relative to those in a lateral row. The rectangular shape is formed with plural rows (only one is shown) of a multiplicity of fibers 42, typically from 10 to 50 rows across the width 'w' of a bundle, measured along the lateral x-axis, and at least as many fibers in each transverse row.

Thus, if there are about 100 fibers closely spaced-apart along the length 'l' of an elongated bundle, measured along the y-axis, and there are about 50 fibers in each lateral row, then the terminal end portions of about 5000 fibers are potted in header 41. The opposed terminal end portions of the elongated fiber bundle are potted in header 41' in a manner analogous to that shown in 41. The open ends of all fibers in headers 41 and 41" point downwards into collection zones in collection pans 43 and 43' respectively, and each header is sealingly bonded around its periphery, to the periphery of each collection pan. Withdrawal conduits 45 and 45' are manifolded to permeate manifold 46 through which permeate collecting in the collection pans is continuously withdrawn. If the permeate is withdrawn in the same plane as the permeate withdrawal conduits 45, 45' and manifold 46, and the transmembrane pressure differential of the fibers is in the range from 35-75 kPa (5-10 psi), manifold 46 may be connected to the suction side of a centrifugal pump which will provide adequate NPSH.

When deployed in a substrate containing suspended and dissolved organic and inorganic matter, the fibers arch upward in a skein which is floatingly buoyed in the substrate with the ends of the fibers anchored in the headers. This is because (i) the permeate is essentially pure water which has a specific gravity less than that of the substrate, and most polymers from which the fibers are formed also have a specific gravity less than 1, and, (ii) the fibers are buoyed by the bubbles. It is critical that these conditions prevail or each fiber in the skein would not acquire the characteristic generally parabolic elongated archway which results when the headers have a narrow rectangular shape.

Within the archway, and directly beneath it, an air-distribution manifold 50 is disposed in a plane below the horizontal plane through the horizontal center-lines of the headers. The manifold 50 is split into two foraminous portions 51 and 51' adjacent headers 41 and 41' respectively, so that when air is discharged through holes in each portion 51 and 51', bubbles are formed which rise adjacent the ends of the fibers and thereafter flow through the skein.

The type of air manifold is not narrowly critical provided it delivers bubbles in a preferred size range from about 1 mm to 25 mm, and the path of the rising bubbles is intercepted by the fibers above, randomly along substantially the entire length of the fibers, from within the generally parabolic profile of the fibers.

If desired, each portion 51 and 51' may be embedded in the upper surface of each header, and the fibers potted around them, making sure the air-passages in the portions 51 and 51' are not plugged with potting compound.

Figure 3A:
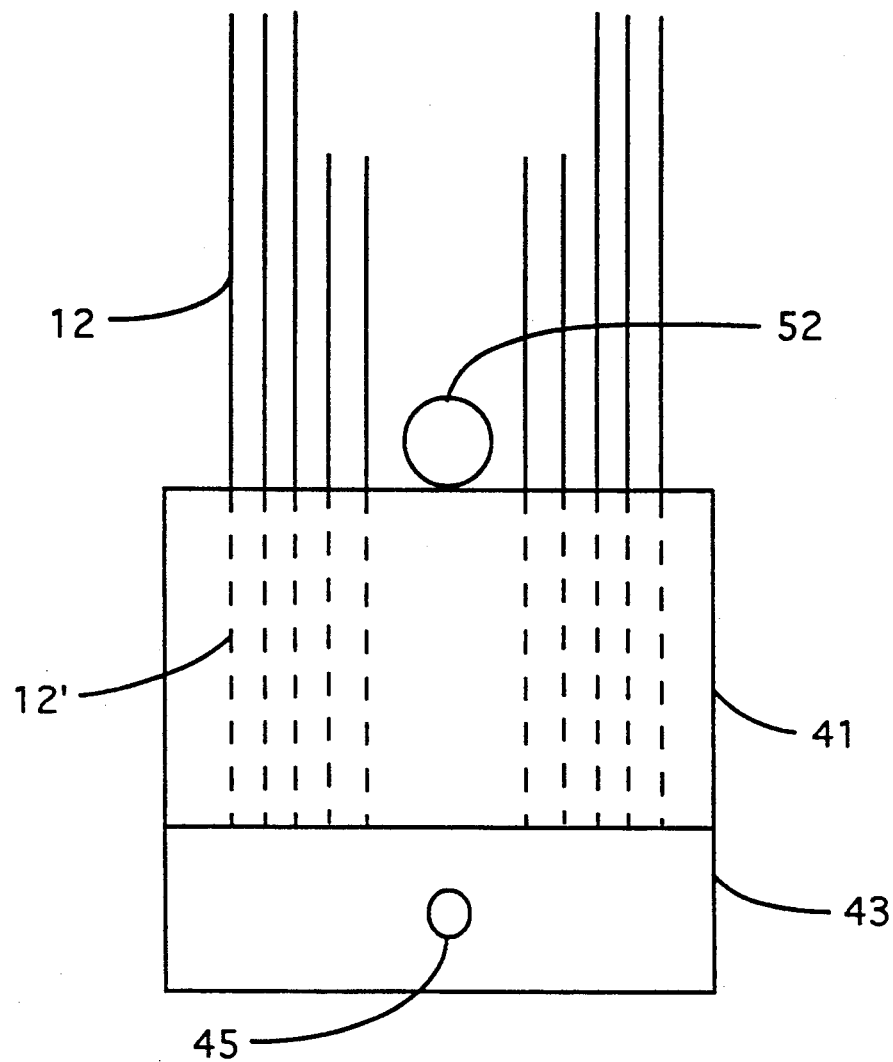
FIG. 3A is a detail, not to scale, illustratively showing a gas distribution means discharging gas between rows of fibers in a header.

Referring to FIG. 3A there is shown a side elevational view of a header 41 fitted with a permeate collection pan 43 from which a permeate withdrawal conduit 45 withdraws permeate. Four rows of fibers 12 with their potted terminal end portions 12' opening into the pan 43, are shown on either side of a gas distribution line 52 which traverses the length of the rows along the base of the fibers. In an analogous manner, a gas distribution line is provided near the base of the opposed terminal end portions of the fibers in the other header of the array. Gas issuing from the line 52, and from the corresponding gas line in the opposed base of the fibers of the skein, effectively aerates the entire skein.

It will be apparent that in general, the fibers will protrude from the upper surface of each header, and the upper surface will be a fiber-supporting surface; and that, the lower surface of each header will contain the open ends of the potted fibers so that each lower surface will be a permeate-discharging surface. However, it will be equally apparent that any surface of the header can function as the fiber-supporting surface, and another surface of each header may function as the permeate-discharging surface, though for obvious reasons, the upper surface is well suited to be the fiber-supporting surface, and the lower surface the permeate-discharging surface. Whichever surfaces are chosen for each function, it will be evident that the permeate is withdrawn through each of the headers.

The air may be provided continuously or intermittently, better results generally being obtained with continuous air flow. The amount of air provided depends upon the type of substrate, the requirements of the type of microorganisms, if any, and the susceptibility of the surfaces of the fibers to be plugged. In general, the amount of air provided is in the range from 0.1 L/sec/L-10 L/sec/L of substrate, measured at standard temperature and pressure, there always being sufficient air to produce desired growth of the microorganisms.

Figure 4:
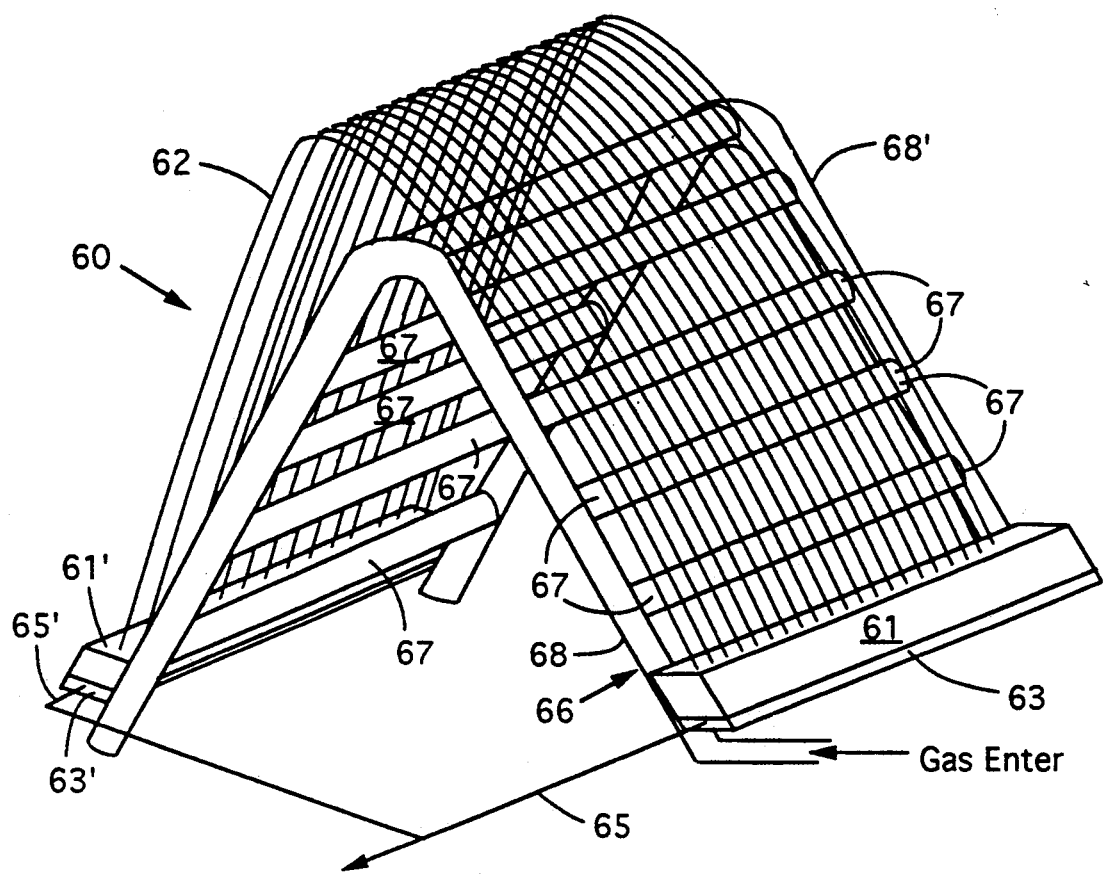
FIG. 4 is a perspective view of another embodiment of the scrubbing-assembly showing an arched foraminous gas-distribution means directly beneath an elongated archway of fibers, the former positioned to maintain a preferred distance relatively close to the fibers to ensure that they remain awash with bubbles generated directly beneath them.
Figure 4A:
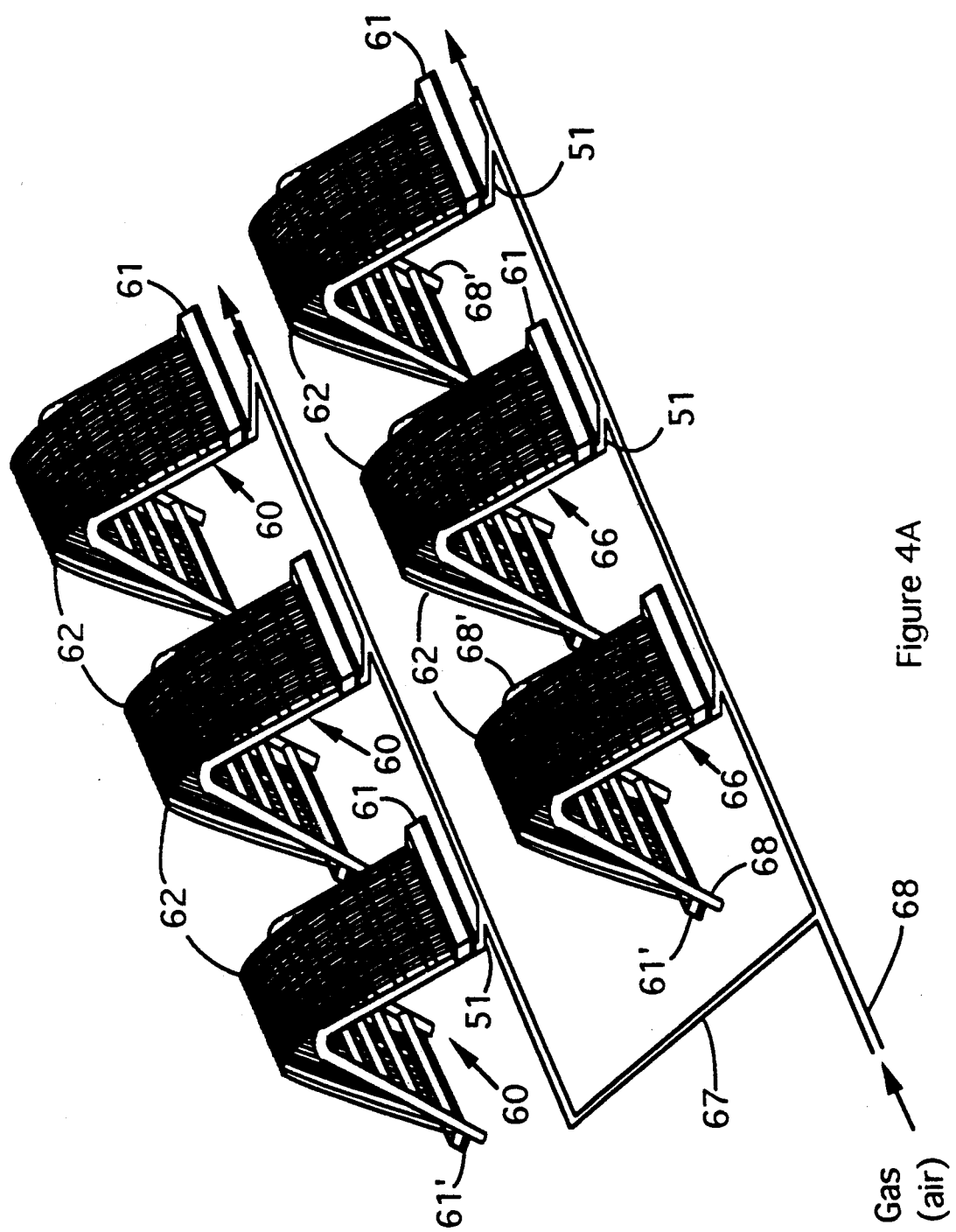
FIG. 4A is a perspective view of a bank of plural scrubbing-assemblies such as the one shown in FIG. 4, as they would be deployed in a large reservoir.

Referring to FIG. 4, there is schematically illustrated another embodiment of an assembly indicated generally by reference numeral 60 which may be used to retrofit a large, deep tank from which permeate is to be withdrawn without using a pump. Typically a bank of assemblies is used in side-by-side relationship within a tank as shown in FIG. 4A. Each assembly 60 with a skein of fibers 62 (only a single row of the multiple, randomly positioned rows is shown for the sake of clarity) is deployed between headers 61 and 61' in a substrate 'S' held in a deep tank (not shown) in which a depth of about 4 meters is maintained. As before, the headers 61 and 61' are secured in fluid-tight relationship with collection zones in collection pans 63 and 63' respectively. Each pan has withdrawal conduits 65 and 65' protruding from the bottom of each pan, and these conduits are manifolded for removal of the permeate.

Because of the depth of the tank, the length (between headers) chosen for each fiber is about 2 m-4 m and the apex of each parabolic arch is just beneath the surface of the substrate. To provide the requisite amount of air efficiently, an A-shaped gas-distribution manifold, indicated generally by reference numeral 66, made of porous pipe, is arched so that air passing through the porous pipe is bubbled through the skein from relatively close range, from 1 cm near the base, to about 50 cm near the apex. The A-shaped manifold 66 comprises plural horizontal (y-axis) porous rungs 67 which maintain a pair of A-shaped porous gas headers 68 and 68' in spaced-apart relationship.

Due to the liquid 'head' provided by the height of the fibers at their apex, above the plane in which permeate is withdrawn, the permeate flows through withdrawal conduits 65 and 65' under gravity alone. When the tank is drained, the A-shaped manifold supports the long fibers and prevents them from matting on the floor of the emptied tank.

Referring to FIG. 4A is a perspective view of a bank of a rectangular pipe frame 67 through which air is supplied with an air line 68. The headers 41 and 41' of each array are secured to each A-shaped air-distribution manifold, on the outer surface thereof, so that the fibers are free to float and sway, and the withdrawal conduits are commonly manifolded (not shown), the more the arrays used, the greater the flow of permeate. Each array assembly is then lowered into the tank and if permeate is to be withdrawn under gravity alone, a connection to the manifolded permeate withdrawal conduits is made through the side wall of the tank.

Figure 5A:
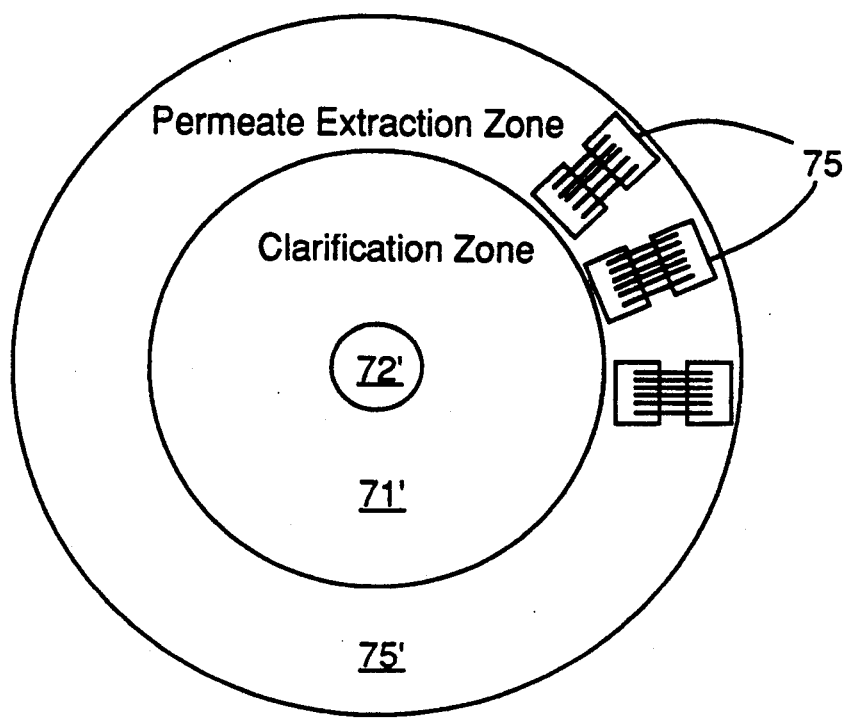
FIG. 5A is a plan view of the tank of FIG. 5, showing an annular permeate withdrawal zone surrounding a central clarification zone.
Figure 5:
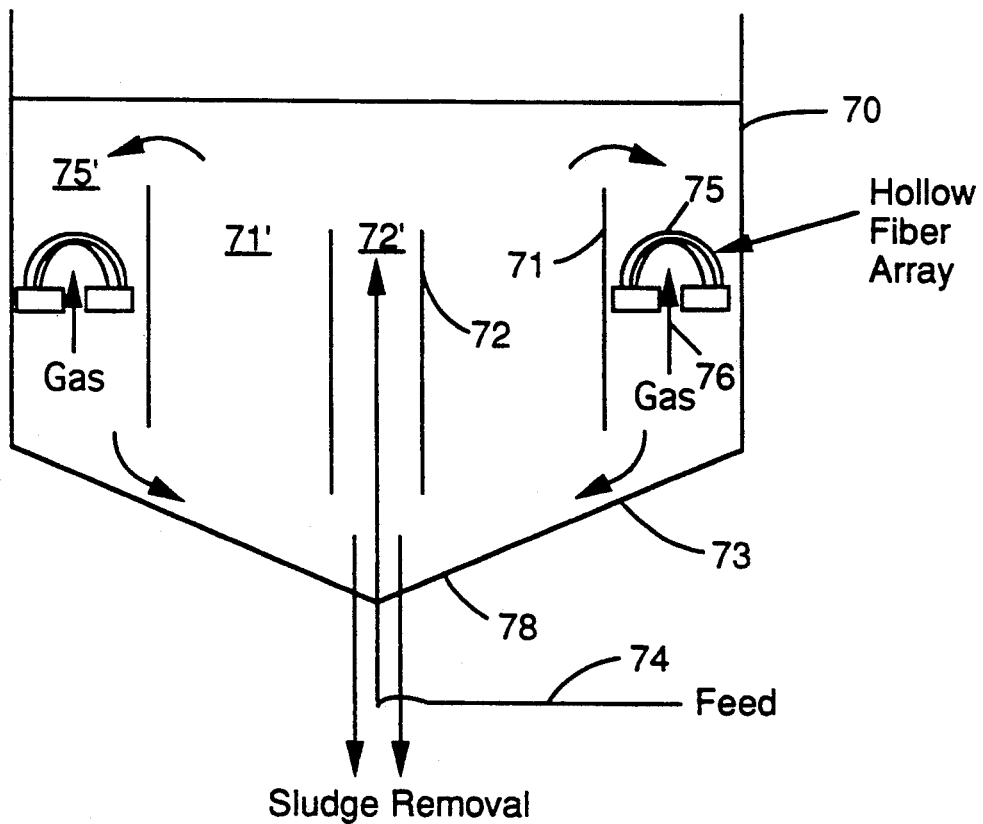
FIG. 5 is an elevational view of a conventional clarifier tank diagrammatically illustrating how several scrubbing-assemblies of membrane device and gas distribution means may be deployed in the clarifier to integrate the function of the membranes with that of the clarifier.

Another embodiment of the invention, in which a conventional clarifier is retrofitted with plural arrays is schematically illustrated in the elevational view shown in FIG. 5. The clarifier tank is a large circular tank 70 provided with a vertical, circular outer baffle 71, a vertical circular inner baffle 72, and a bottom 73 which slopes towards the center (apex) for drainage of accumulating sludge. The baffles may be individual, closely spaced rectangular plates arranged in outer and inner circles, but continuous cylindrical baffles (shown) are preferred. Irrespective of which baffles are used, the baffles are located so that their bottom peripheries are located at a chosen vertical distance above the bottom. Feed is introduced through feed line 74 in the bottom of the tank 70 until the level of the substrate rises above the outer baffle 71.

Plural arrays 75 are deployed with suitable mounting means in an outer annular permeate extraction zone 75' (FIG. 5A) formed between a circular outer baffle 71 and the wall of the tank 70, at a depth sufficient to submerge the freely floating fibers. A clarification zone 71' is defined between the outer circular baffle 71 and an inner circular baffle 72. The inner circular baffle 72 provides a vertical axial passage 72' through which substrate is fed into the tank 70. The arrays form a circular archway (see FIG. 5A) in the permeate extraction zone 75' and an air manifold 76 is positioned within the archway in such a manner as to contact essentially the entire surface of each fiber in the skeins of fibers with bubbles which wash over the fibers continuously. The permeate is withdrawn through a permeate manifold (not shown) through the side of the tank, or through the open apex 78 in the bottom of the tank through which apex sludge is removed.

The permeate may be withdrawn over the side of the tank, if desired, using a slight NPSH, less than 2 m of head, for a centrifugal pump. Once flow of permeate is started, it can be maintained without the pump because of the siphoning effect, as long as the level of substrate in the tank is maintained and the permeate is withdrawn below the level of the substrate.

Figure 6:
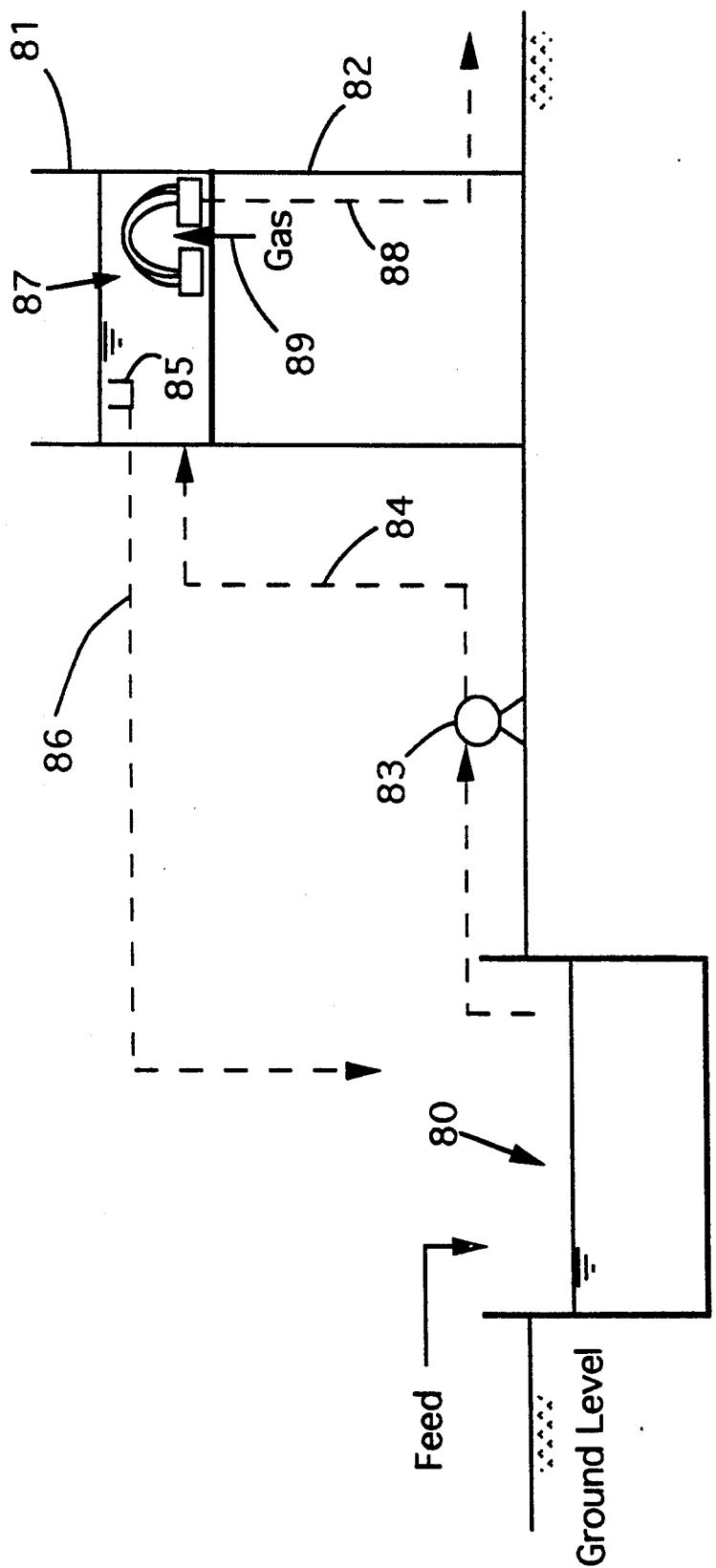
FIG. 6 is an elevational view schematically illustrating how a bank of membrane devices (only one is shown) may be used in an elevated tank to withdraw permeate without using a vacuum pump.

Since an accumulation of air bubbles in the permeate withdrawal conduit might stop siphoning action, reliance upon such action may be avoided by elevating the substrate tank relative to the location where the permeate is withdrawn into atmospheric pressure. An arrangement for doing so is schematically illustrated in FIG. 6 in which conventional aeration of the substrate, flowing into the tank through a feed line (not shown), is performed in a large aeration tank 80 in which the level of substrate is essentially at ground level.

An elevated tank 81 is positioned on tank stanchions 82, at a height such that the level of substrate in the tank 81 will be from about 5-7 m above ground level. A centrifugal sump pump 83 delivers preliminarily aerated substrate through line 84 to the tank 81 which is provided with an overflow weir 85 for return of substrate to the tank 80 through return line 86. Plural assemblies 87 (only one is shown) are positioned in the tank with provision for supplying air to an air-distribution manifold 89 which supplies air to individual air distributors (not shown) under each skein of fibers, thus providing secondary aeration for the substrate.

In this manner, a relatively small tank may be used to provide optimum aeration not only for the requirements of the microbes but also to keep the surfaces of the fibers clean. Permeate from the assemblies is withdrawn from each through a permeate line 88 which discharges permeate at ground level.

Figure 7:
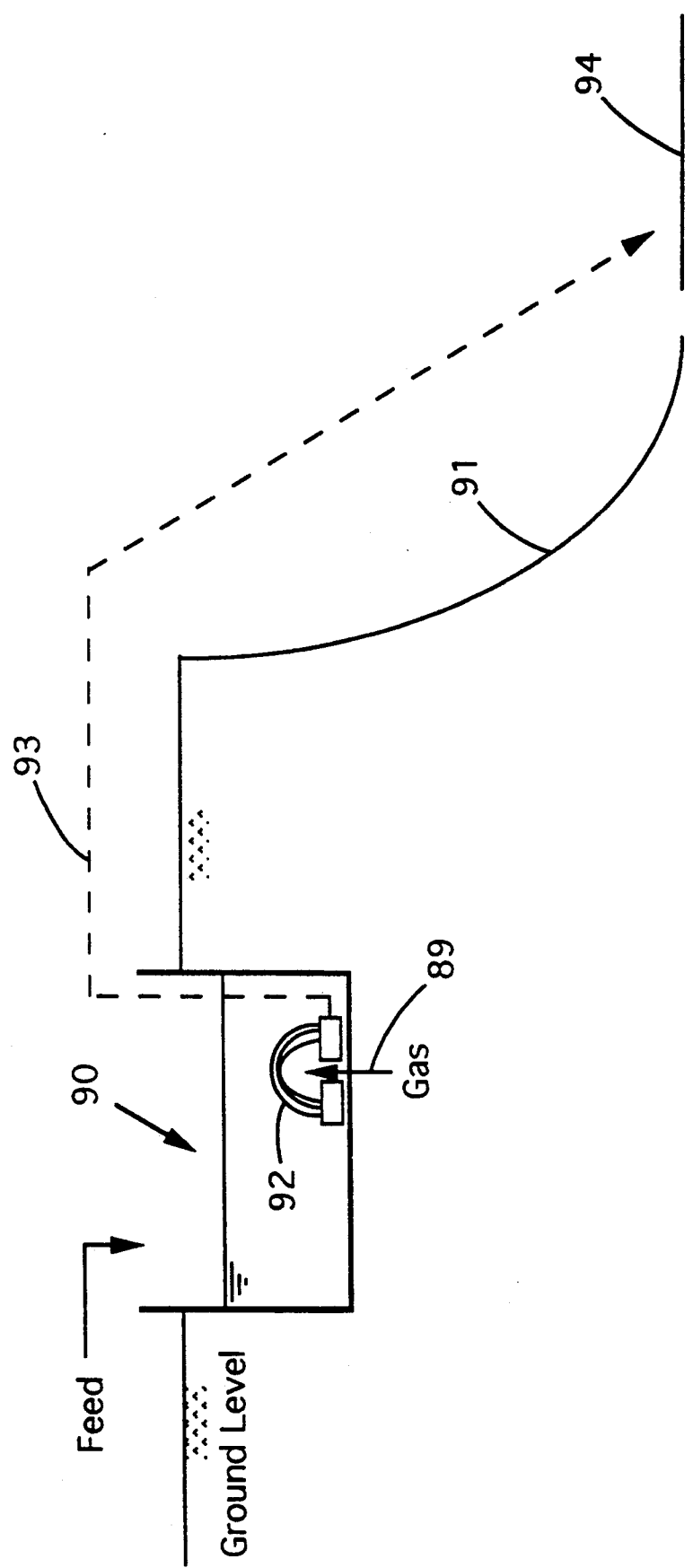
FIG. 7 is an elevational view schematically illustrating how a bank of membrane devices may be used in a recessed tank to withdraw permeate without using any pump.

Another embodiment which avoids using any pump to withdraw permeate, is diagrammatically illustrated in FIG. 7 where a large in-the-ground tank 90 is positioned near the edge of an incline 91. In a manner analogous to that described for the assemblies in FIG. 4 above, plural assemblies 92 (only one is shown) are deployed in the tank, and provided with an air-distribution means (not shown) which supplies enough air beneath each skein of fibers to keep essentially the entire surface of all the fibers in the skein awash with bubbles. Permeate is withdrawn through a permeate manifold 93 which discharges the permeate at the bottom 94 of the incline, enough below the level of substrate in the tank to overcome the atmospheric 'head'. This head is typically from 5-7 m.

Figure 8:
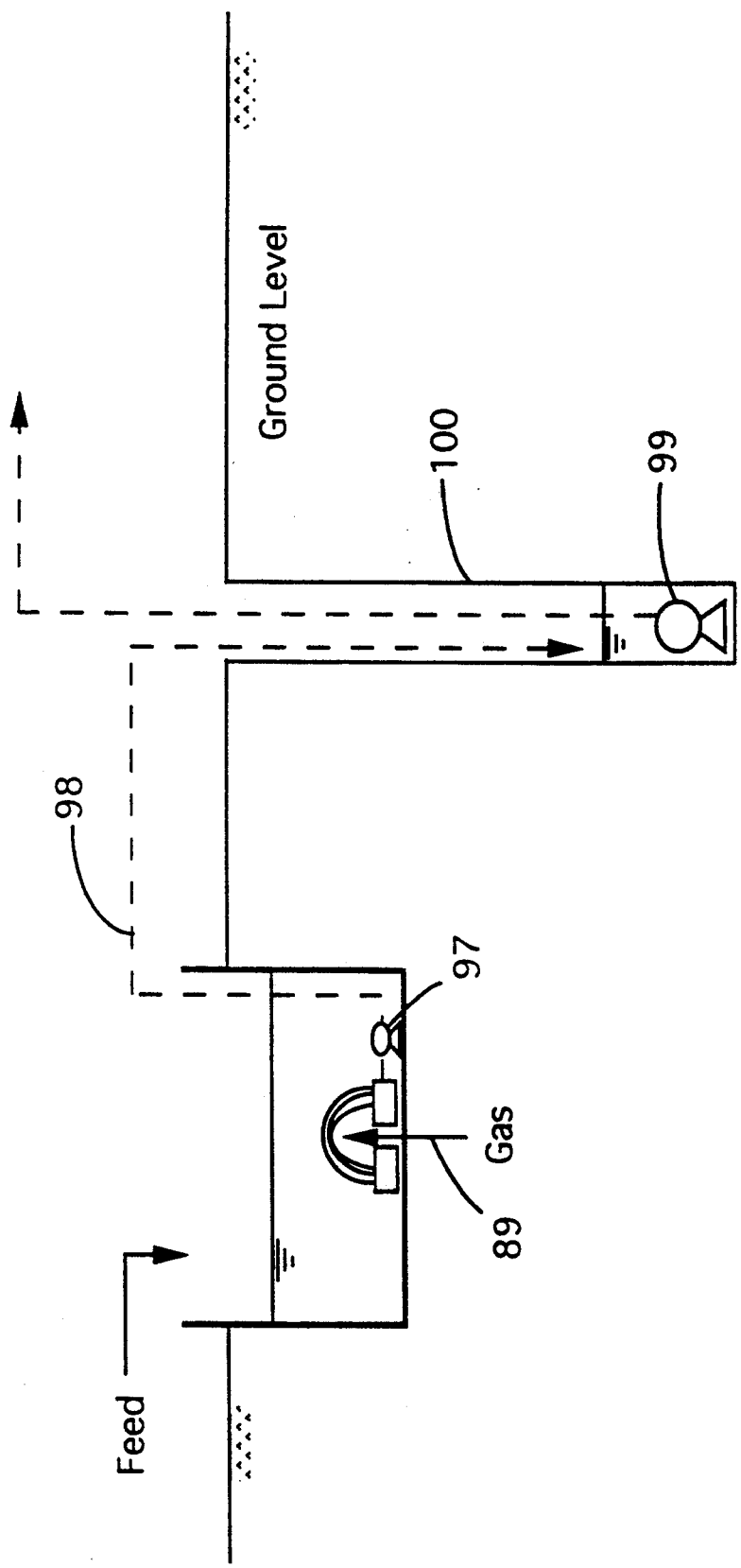
FIG. 8 is an elevational view schematically illustrating another embodiment in which a bank of membrane devices may be used in a recessed tank to withdraw permeate with a flow-through pump, not a conventional vacuum pump.

Still another embodiment illustrating removal of permeate without using a vacuum pump, is shown in FIG. 8 where plural assemblies 96 are deployed in an in-the-ground tank 95 which is aerated with an air-distribution manifold (not shown) supplying air beneath each skein of fibers of each assembly. The suction side of a sump pump 97 is placed in open fluid communication with a permeate header (not shown) which collects the permeate from all the assemblies 96 and discharges it through line 98.

To avoid using a sump pump within the tank, one may place a centrifugal pump 99 in a well 100, bored near the tank. In this arrangement, initially, the pump must overcome only the slight head of the height above the substrate level at which the line to the suction side of the pump is looped. Once operation is commenced, the permeate is supplied to the pump by the siphon effect.

Figure 9A:
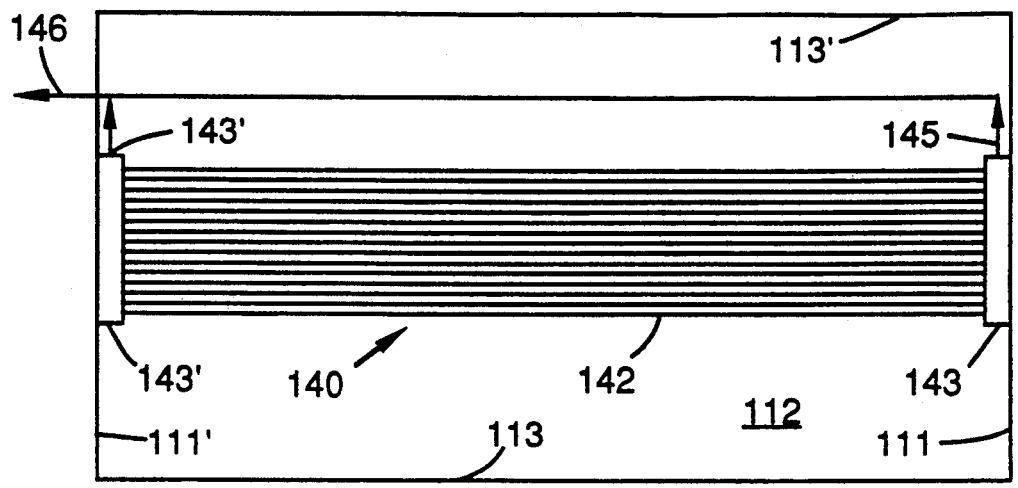
FIG. 9A is a plan view schematically illustrating how the headers of the single frameless array in FIG. 9 (the others are not shown), are mounted against the sides of the tank.
Figure 9:
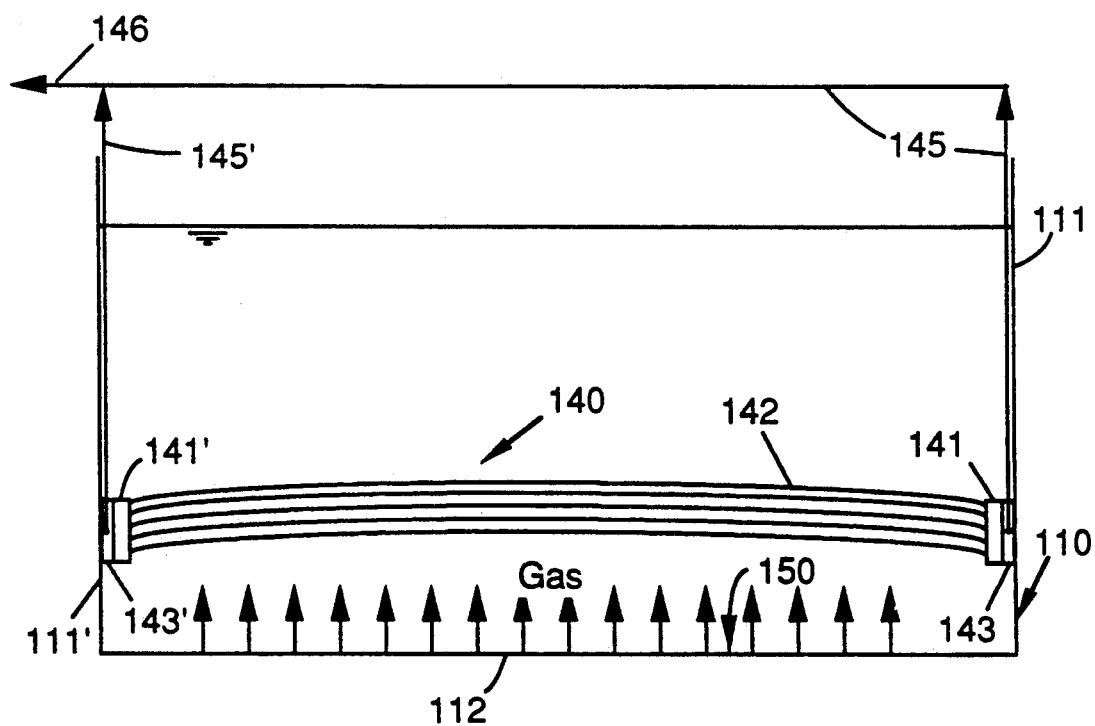
FIG. 9 is an elevational view schematically illustrating another embodiment in which a bank of assemblies are submerged in a tank, except that only one of the several assemblies is shown, each directly behind the other to form the bank, in combination with a gas-distribution means directly beneath each array. Fibers are buoyantly suspended above the horizontal plane through the horizontal center-line of a header; permeate may be withdrawn, with or without the use of a vacuum pump, depending upon how high above the ground the tank is supported.
Figure 10:
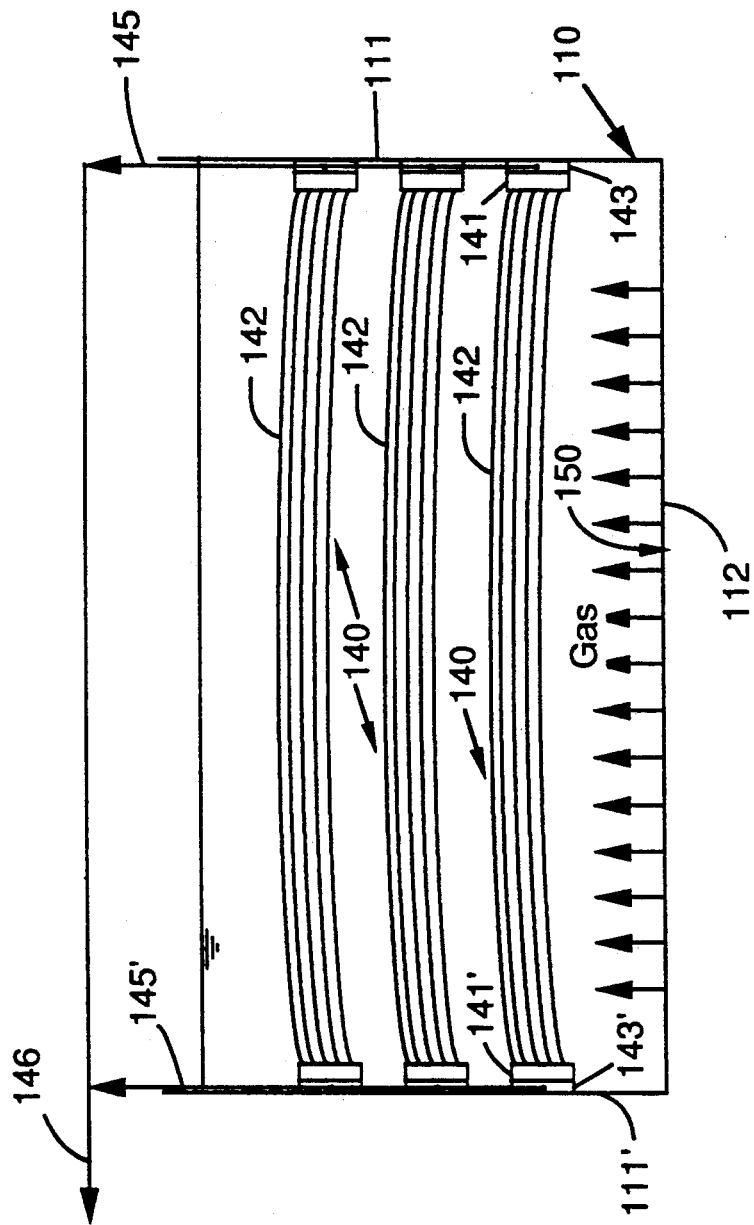
FIG. 10 is an elevational view schematically illustrating another embodiment in which a scrubbing assembly may be submerged in a tank to withdraw permeate, with or without using a vacuum pump, depending upon the transmembrane pressure differential of the fibers and how high off the ground the tank is supported.

Referring to FIG. 9, there is illustrated a large, rectangular tank indicated generally by reference numeral 110, having opposed upstanding side walls 111 and 111', and a bottom 112. The sides 111 and 111' are about 3 m apart. One of several arrays, indicated generally by reference numeral 140, comprises hollow fibers 142 securely held in opposed headers 141 and 141' which communicate with permeate pans 143 and 143'. As shown, the fibers are shown in relatively flat parabolic arcs because the length of the fibers between the headers is less than would normally be used to maximize the membrane area in the available space. The reason for the shortened fibers is to minimize entanglement with adjacent arrays, not only those on either side, but those above and beneath, if plural banks are used, as is shown in FIG. 10. The pans 143 and 143' are removably mounted with suitable mounting means against the sides, so that permeate is withdrawn into permeate headers 145 and 145' on either side, which combine into the permeate discharge 146.

Within a zone directly beneath, and relatively proximately disposed to the fibers is an air distribution means indicated generally by reference numeral 150. Typically, an air distribution line will be placed directly beneath each array, all the lines being manifolded to the air-distribution means 150.

It will be evident that if the tank is at ground level, there will be insufficient liquid head to induce a vacuum under gravity alone, so a pump will be used to produce the necessary suction. Such as a pump should be capable of running dry for a short period, and of maintaining a vacuum on the suction side of from 25.5 cm (10")−51 cm (20") of Hg, or −35 kPa (−5 psi) to −70 kPa (−10 psi). Examples of such pumps rated at 18.9 L/min (5 gpm) @15" Hg, are (i) flexible-impeller centrifugal pumps, e.g. Jabsco #30510-2003; (ii) air operated diaphragm pumps, e.g. Wilden M2; (iii) progressing cavity pumps, e.g. Ramoy 3561; and (iv) hosepumps, e.g. Waukesha SP 25. Of course, the higher the vacuum produced by the pump, the better the flux, but in a low cost operation, the cost of the vacuum pump and its operation is usually unjustifiable.

Referring to FIG. 9A is shown a plan view of the single array shown in FIG. 9, with the front wall 113 and the rear wall 113'. The side walls 111 and 111' are shown with a break, to reinforce the fact that there will typically be as many assemblies in a tank as it can hold, so that essentially the entire area of the tank is covered with fibers.

Because the operation of the system is so inexpensive, the cost of using a very large membrane area can be justified. To install additional membrane area, a second bank of arrays may be installed in the tank.

Referring to FIG. 10 there is shown three banks of arrays 140, one above the other, which is especially well-suited for a deep tank, the arrays and pans of each bank being mounted against the sides of the tanks, one array directly behind another. As before the air distribution means 150 is placed in the bottom of the tank directly beneath the arrays. If oxygen-enriched air is available, it may be used instead of air to satisfy the demands of the growing mass of microorganisms.

Figure 11:
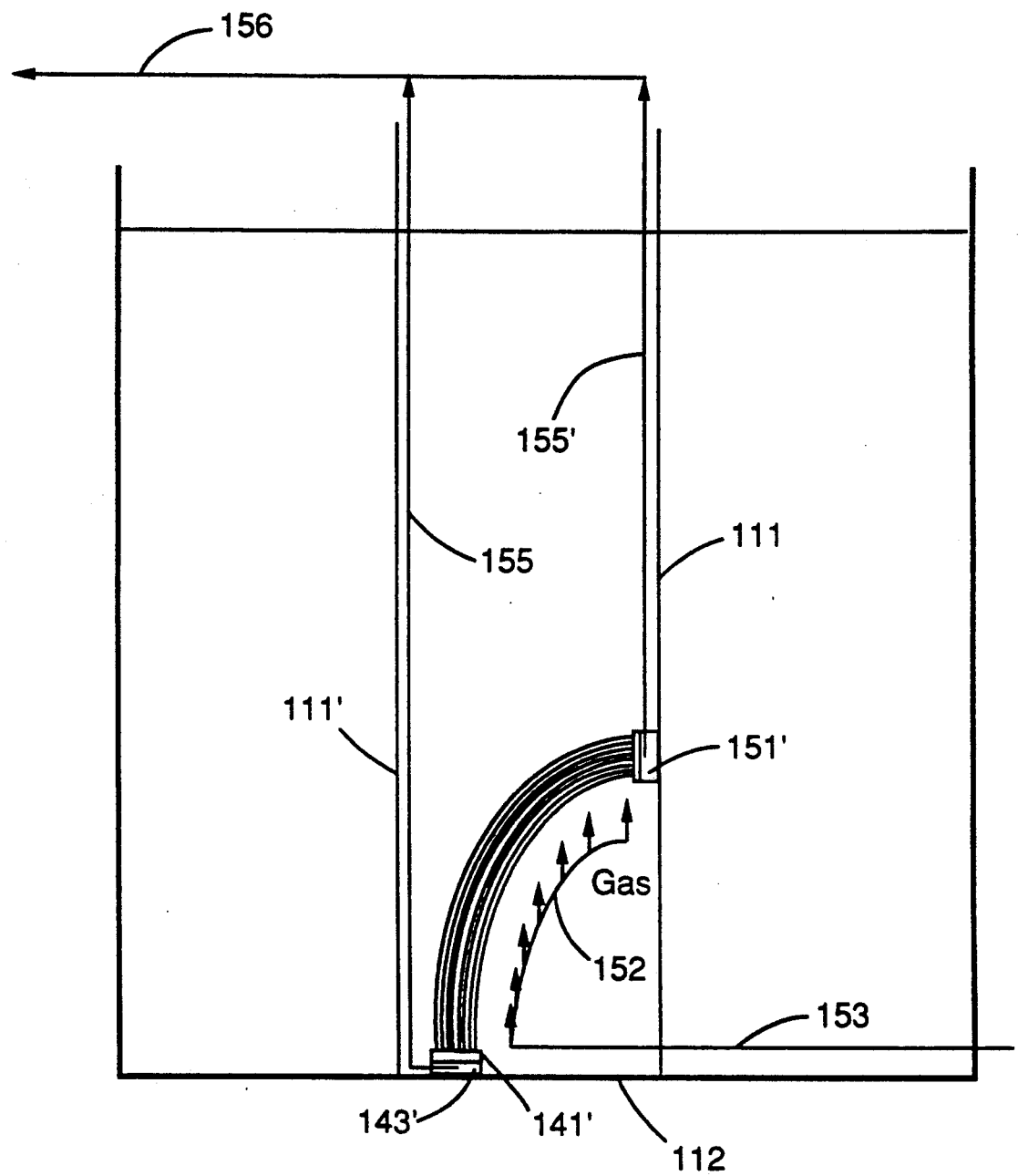
FIG. 11 is an elevational view schematically illustrating yet another embodiment in which a scrubbing assembly is submerged at an acute angle in a relatively deep tank to take advantage of the available space and to minimize growth of microorganisms on the fibers.

Referring to FIG. 11 there is shown another embodiment of an assembly in a deep tank, in which a single array 150 with longer fibers than the width or diameter of the tank, may provide adequate surface area, and banks of arrays as shown in FIG. 10 could not be justified. As indicated, the array 150 is inclinedly disposed within the tank with one header and collection pan, together indicated by reference numeral 151 mounted on one wall near the bottom of the tank, and the other header and collection pan 151' mounted transversely on the opposite wall of the tank, so that a horizontal plane through the horizontal center line of the upper header 151' is vertically spaced-apart from the horizontal plane through the horizontal center line of the lower header 151. As before, permeate withdrawal lines 155 and 155' are connected to the collection pans, and combined for withdrawal through line 156.

An arcuate porous gas-distribution means 152 is mounted directly beneath the fibers of the array 150, to provide gas to scrub the fibers, and is connected through the line 153 to a source of gas.

In each of the embodiments illustrated hereinabove, it will be seen that if a pump is used at all, it is not a vacuum pump. Therefore, the cost of a vacuum pump, its operation and maintenance is avoided. However, it will be evident that if a vacuum pump were used to generate a higher vacuum than 50 cm of Hg, or even a higher vacuum than is induced under gravity, the flux would be enhanced, and in those instances where a high flux is demanded, the cost of a vacuum pump may be justified.

The following illustrative examples using the invention to treat a wastewater stream containing submicron size particles of silica, and also, in a conventional activated sludge process. Other embodiments of the invention directed to a different separation problem will employ analogous arrays and processes.

EXAMPLE 1—ULTRAFILTRATION

Activated sludge, with growing microorganisms in it, is flowed at the rate of 20 L/day, at 25° C. into a 100 L pilot plant tank holding 80 L. A single frameless array (1.1 $m^2$ surface area) configured as shown in FIG. 3, is submerged in the tank so that the apex of each of the fibers is just below the surface of the liquid in the tank. The total suspended solids in the activated sludge is 17.5 g/L (1.72%), and volatile suspended solids are 15 g/L (1.48%)

The frameless array is made with a skein of 200 polysulfone, microporous hollow ultrafiltration fibers having an outside diameter of 2 mm, a wall thickness of about 1 mm, a surface porosity of about 40% and a pore size of about 0.07 μm, both latter physical properties being determined by PEG (polyethylene glycol) molecular weight cut-off which is about 70,000. The opposed ends of the fibers are potted in first and second headers respectively. Each header is a 2.5 cm long half-cylindrical section of a 5 cm diameter cylinder of epoxy resin in which the terminal portions of the fibers were potted to an average depth of about 1.5 cm. The average transmembrane pressure differential is about 25 kPa (3.6 psi).

Permeate withdrawal lines are connected to the collection pan of each header and each is subjected to 34.5 kPa (5 psi) suction. An air sparging line is used to generate bubbles in the range from 1 mm to 5 mm in diameter which are discharged about 75 cm below the top of the skein. The flow rate of air is most preferably in the range from 40 $m^3$/day/$m^2$ to 75 $m^3$/day/$m^2$. 0.57 $m^3$/hr (20 SCFH) of air is used for the 0.3 $m^2$, which is sufficient not only for oxidation requirements of the biomass, but also for membrane "gas scrubbing", or, "air scrubbing", if air is used.

Figure 12:
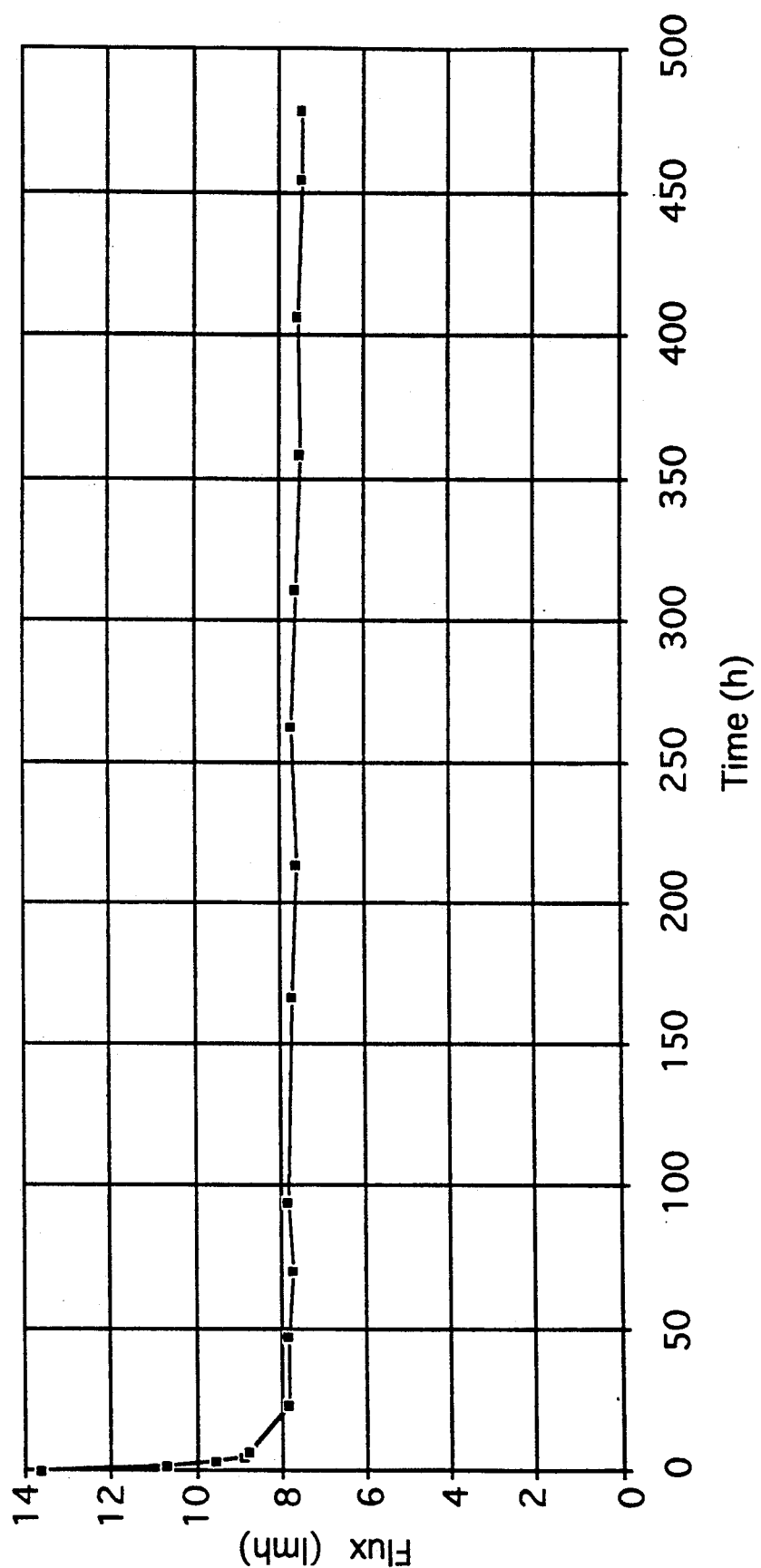
FIG. 12 is a graph in which the variation of flux is plotted as a function of time, for the membrane device constructed with ultrafiltration hollow fiber membranes.

Permeate withdrawn has an average reading of <0.1 NTU (nephelometric turbidity units), which is substantially clear to the naked eye. The amount of permeate withdrawn during specified intervals is measured and plotted in FIG. 12 as flux (liters-meter$^2$-hr, "LMH") as a function of time. At the outset, the amount of permeate withdrawn over 6 hr intervals is measured; thereafter, intervals are progressively lengthened to 12 hr, 24 hr, and finally about every 48 hr, as indicated by the points plotted on the graph.

It is seen that the flux is nearly 14 LMH at the outset, but drops sharply during the first day to about 8 LMH. Thereafter, the flux remains substantially constant, as is evidenced by the relatively flat slope of the curve starting at nearly 8 LMH after the first day. The test is terminated at the end of 19 days.

EXAMPLE 2—MICROFILTRATION

A microfiltration test is conducted with polysulfone microfiltration fibers in a second array having the same total surface area as the first array in Example 1, and under the same process conditions, to determine the flux as a function of time.

The second frameless array of polysulfone microfiltration hollow fibers is placed in the same pilot plant tank as the first array and subjected to the same "air scrubbing" and flow rate of sludge. The second array has fibers with an outside diameter of 1 mm, a wall thickness of about 0.5 mm, a surface porosity of about 40% with pores about 0.1 $\mu$m in diameter, both latter physical properties being determined by a molecular weight cut off 100,000. The array is configured in a manner analogous to the first array used in example 1 hereinabove, to provide the same total surface area of 1.1 m$^2$. The same pilot plant tank is used as was used in the previous example and The frameless array is made with a skein of 200 polysulfone, microporous hollow microfiltration fibers and a pore size of about 0.1 $\mu$m, both determined by PEG molecular weight cut-off which is about 100,000. The opposed ends of the fibers are potted in first and second headers respectively. Each header is a 45 cm long half-cylindrical section of a 5 cm diameter cylinder of epoxy resin in which the fibers were potted to a depth sufficient to have their open ends protrude from the bottom of the header. Each header has the ends of 400 fibers potted in it because the smaller diameter of the 1 mm fibers provides one-half the area of the 2 mm diameter fibers, for a skein having the same total surface area of 1.1 m$^2$. The average transmembrane pressure differential is about 25 kPa (3.6 psi).

Permeate withdrawal lines are connected to the collection pan of each header and each is subjected to 34.5 kPa (5 psi) suction. Air is provided directly beneath the skein at 0.57 m$^3$/hr (20 SCFH) which is sufficient not only for the oxidation requirements of the biomass but also for membrane "air scrubbing".

Figure 12A:
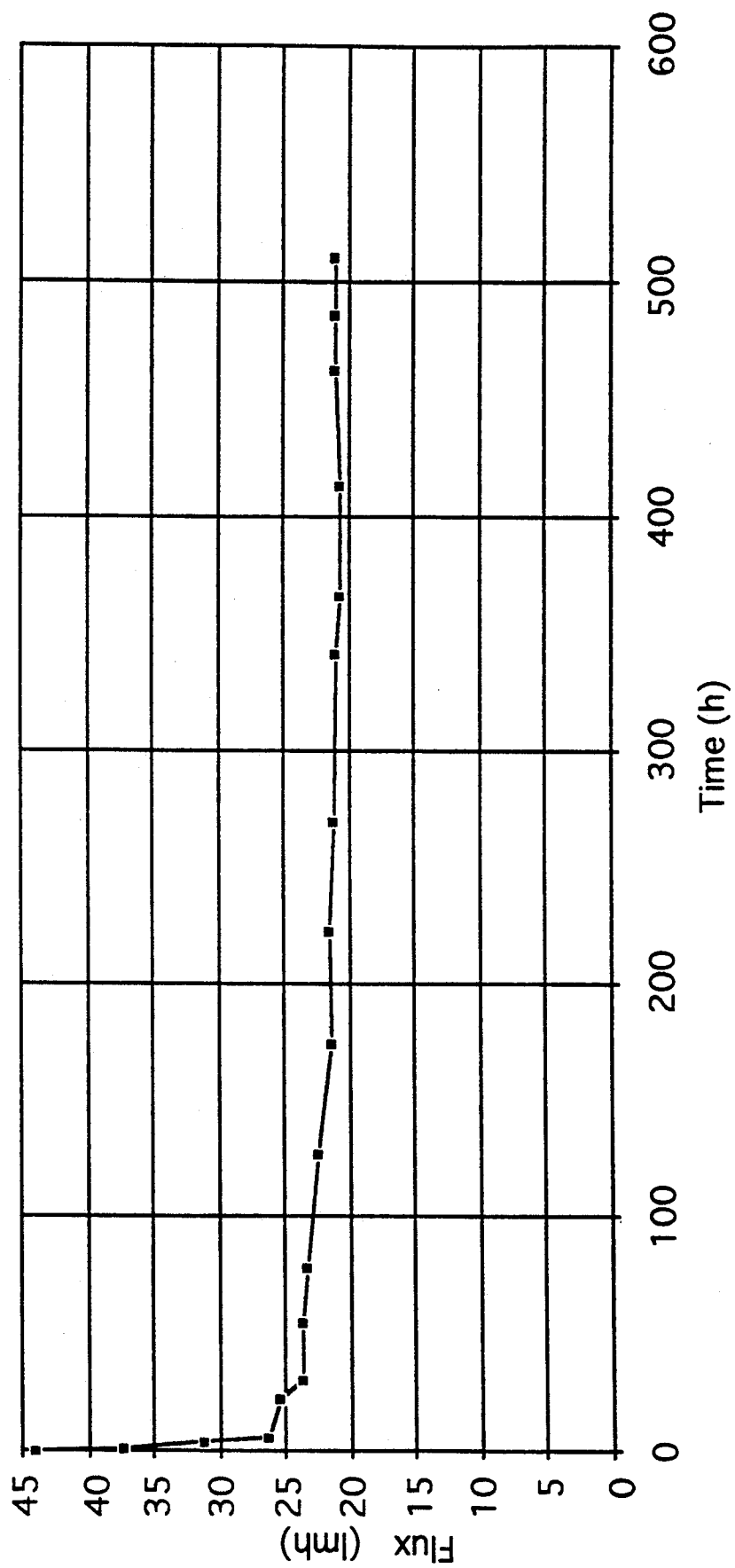
FIG. 12A is a graph in which the variation of flux is plotted as a function of time, for the membrane device constructed with microfiltration hollow fiber membranes.

Permeate withdrawn has an average reading of <0.5 NTU which is barely discernible to the naked eye. As before, the amount of permeate withdrawn during specified intervals is measured and plotted in FIG. 12A as flux (LMH) as a function of time.

It is seen that the flux is 45 LMH at the outset, but drops sharply during the first day to about 25 LMH. Thereafter, the flux remains substantially constant, as is evidenced by the relatively flat slope of the curve after the first day, showing a flux of >20 LMH without any indication of decreasing after three weeks, when the test is stopped.

EXAMPLE 3

Comparison of results obtained with an assembly of a frameless array with an air distributor means, with results obtained using an assembly configured as disclosed by Yamamoto et al. in Wat. Sci. Tech. Vol. 21, Brighton pp 43-54, 1989:

This experimental comparison was conducted using two essentially identical frameless arrays in essentially identical 80 L tanks filled with the same activated sludge substrate. The only differences between the stated experiment of Yamamoto et al., and that of the applicants are: (i) the configuration of the fibers in Yamamoto's experiment are inverted relative to those in the frameless array; (ii) to keep the array inverted in the Yamamoto et al. array, the fibers were tied to a wire framework (to keep the fibers below a plane containing the headers); and, (iii) the air for the Yamamoto et al. replication was discharged from an aerator, but the air for the frameless array was discharged from a diffuser with 200 $\mu$m openings. The rate of air introduced is taken from Chiemchaisri et al.

A first frameless array of 280 individual fibers, each 0.75 m long, with an (ID) inside diameter of 0.4 mm and an OD of 0.46 mm, pore size 0.04 $\mu$m, PEG molecular weight cutoff 100,000 and having a total surface area of 0.3 m$^2$, were suspended beneath the header in a first 80 L tank containing 40 L of the substrate, and the fibers were tied in spaced-apart position in an inverted generally parabolic form (referred to hereunder as "inverted parabolic form"). The fibers were of Celgard polypropylene (hydrophobic in nature, similar to those used by Yamamoto et al.). Each header was 5 cm in diameter and about 45 cm long.

The Yamamoto et al. air supply was replicated with a jet aerator using three in-line aspirators (venturi) each having a maximum free air pumping capacity of 11.5 L/min at a water consumption rate of 6.5 L/min, and each provided with a perforated vertical discharge leg, with about 250 $\mu$m diameter holes, through which a mixture of water and air was discharged forming air bubbles which were about 1 mm in diameter. The air was supplied at 300 kPa (30 psig) and the bubbles were discharged from the side of the tank towards its center, and aimed at the frameless array. The flow rate of air was measured with a flow meter as being 34.5 L/min (72 SCFH) so that the flow rate of air across the fibers was 2.05 m$^3$/hr/m$^2$.

A second identical frameless array was placed in the second tank so that the fibers were buoyantly freely swayable in the substrate in a generally parabolic form.

Air for the second frameless array in parabolic form, was supplied at 136 kPa (5 psig) with a tubular air distributor having 200 $\mu$m openings. Less air is used for the second array because the larger bubbles do not require as high a flow rate of air as a jet aerator. The flow rate of air was measured with a flow meter as being 0.1 L/min (20 SCFH) so that the flow rate of air across the fibers was 0.57 m$^3$/hr/m$^2$.

It will be evident from FIG. 1 in which the flux is plotted as a function of operating time for the two cases, that the flux for the parabolic frameless array, identified as reference numeral 1, and that for the inverted parabolic array identified by 2, are is essentially the same for each case, as one would expect. However, after about 50 hr, it is seen that the flux for the parabolic array reaches an equilibrium, while that for the inverted parabolic array keeps declining.

The evidence shows that, even when using the identical array, the fibers must be buoyantly swayable, or, that the smaller bubbles generated by the jet aerator do not have the force to be effective, or both.

It will now be evident that the membrane device and basic separation processes of this invention may be used in the recovery and separation of a wide variety of commercially significant materials, some of which, illustratively referred to, include the recovery of water from ground water containing micron and submicron particles of siliceous materials; or, the recovery of solvent from paint-contaminated solvent. In each application, the choice of membrane will depend upon the physical characteristics of the materials and the separation desired. The choice of gas will depend on whether oxygen is needed in the substrate. To "gas scrub" fibers in a siliceous water substrate, carbon dioxide may be used.

In each case, the simple process comprises, disposing a frameless array of a multiplicity of hollow fiber membranes, or fibers each having a length $>0.5$ meter, together having a surface area $>1$ m$^2$, in a body of substrate which is unconfined in a modular shell, so that the fibers are essentially freely swayable in the substrate. The substrate is typically not under pressure greater than atmospheric. The fibers have a low transmembrane pressure differential in the range from about 3.5 kPa (0.5 psi) to about 350 kPa (50 psi), and the headers, the terminal portions of the fibers, and the ends of the fibers are disposed in spaced-apart relationship as described hereinabove, so that by applying a suction on the lower face of at least one of the headers, preferably both, permeate is withdrawn through the collection means in which each header is mounted in fluid-tight communication. Depending upon the relative orientation of the array and the location from which the suction is applied, the permeate may be withdrawn under the vacuum generated by gravity.

From the foregoing it will now be evident that the membrane device of this invention is specifically directed to the use of membranes having a transmembrane pressure differential in the range from about 0.7 kPa (0.1 psi) to about 345 kPa (50 psi), and that this specification effectively indicates that the membranes will have pores in the size range from about 0.001 μm–0.1 μm, there being some overlap between ultrafiltration and microfiltration membranes. The former are generally in the range from 0.001 μm to about 0.1 μm; and the latter (microfiltration) in the range from about 0.1 μm to about 1.0 μm. At the low end of the range it will be recognized that the transmembrane pressure differential will generally be quite high, requiring the use of a vacuum pump and a reservoir maintained under elevated pressure.

Having thus provided a general discussion, and specific illustrations of the best mode of constructing and deploying a membrane device comprising a frameless array of long fibers in a substrate from which a particular component is to be produced as permeate, teaching how the device is used in an assembly with a gas-distribution means, and providing specific illustrative systems and processes in which the assembly is used, it is to be understood that no undue restrictions are to be imposed by reason of the specific embodiments illustrated and discussed, and particularly that the invention is not restricted to a slavish adherence to the details set forth herein.

We claim:

1. A membrane device, for withdrawing permeate from a multicomponent liquid substrate, comprising,
    means for providing an alternative to a conventional module having plural individual arrays therewithin, including
    a frameless array of a multiplicity fiber membranes, or fibers, for operation without being supported except by said substrate, and without being confined in a shell of a module, said fibers together having a surface area $>1$ m$^2$, said fibers being buoyantly swayable in said substrate, said fibers providing a transmembrane pressure differential in the range from about 0.7 kPa (0.1 psi) to about 345 kPa (50 psi), and each having a length $>0.5$ meter;
    a pair of first and second headers disposed in spaced-apart relationship within said substrate so that said fibers, when deployed, present an arcuate configuration above a horizontal plane through the horizontal center-line of a header;
    said first header having a terminal end portion of each fiber secured therein, and a second header having an opposed terminal end portion of each fiber secured therein, all said fibers extending from a face of each said header and essentially all said fibers being open at their ends so as to discharge said permeate through each of said headers;
    said fibers being sealingly secured with open ends of the fibers secured in fluid-tight relationship with each other in each of said headers;
    liquid collection means to collect said permeate, connected in open fluid communication with said lower face of each of said headers; and,
    means to withdraw said permeate.

2. The membrane device of claim 1 wherein each apex of each arcuate fiber is submerged.

3. The membrane device of claim 1 wherein each said header is a mass of solid synthetic resinous material in which said terminal end portions are potted and said fibers are formed from an organic resinous material or a ceramic.

4. The membrane device of claim 3 wherein each said hollow fiber has an outside diameter in the range from about 20 μm to about 3 mm, a wall thickness in the range from about 5 μm to about 2 mm, and, said fiber is formed from a material selected from the group consisting of natural and synthetic polymers, and pore size in the range from 0.001 μm–1.0 μm.

5. The membrane device of claim 4 wherein said terminal end portions of said fibers are potted within said mass of thermosetting synthetic resinous material to a depth in the range from about 1 cm to about 5 cm, and said headers are removably mounted in transversely and vertically spaced-apart relationship.

6. The membrane device of claim 5 wherein said open ends of fibers are bounded by a geometrically irregular peripheral boundary around the outermost peripheries of the outermost fibers in the boundary, and the length of a fiber is essentially independent of the strength of said fiber, or its diameter.

7. The membrane device of claim 5 wherein said substrate is maintained at a pressure in the range from about 1–10 atm, said fibers extend as a skein upwardly from a fiber-supporting face of each of said headers, said arcuate configuration is generally parabolic, and said fibers extend downwardly through the permeate-discharging face of said headers, and said permeate is discharged downwardly relative to the direction in which said fibers are deployed.

8. The membrane device of claim 5 wherein said fibers together have a surface area in the range from 10 to $10^3$ m$^2$.

9. The membrane device of claim 4 wherein said transmembrane pressure differential is in the range from 3.5 kPa (0.5 psi) to about 175 kPa (25 psi), said fibers are in the range from 0.5 m to 5 m long, and said terminal end portions of said fibers are potted within said a mass of thermosetting synthetic resinous material to a depth in the range from about 1 cm to about 5 cm, and said headers are coplanarly, removably mounted.

10. A gas-scrubbed assembly comprising, means for providing an alterative to a conventional module having plural individual arrays therewithin, including, a membrane device in combination with a gas-distribution means, to minimize build-up of particulate deposits on the surfaces of hollow fiber membranes in said device, and to recover permeate from a multicomponent liquid substrate, said assembly comprising, a frameless array of a bundle of said hollow fibers in a skein which is unsupported for operation in said substrate held at a pressure in the range from 1-10 atm, without being confined in a module's shell, the ends of said fibers being secured in first and second headers adapted to be mounted in spaced-apart relationship within said substrate and beneath said skein which is buoyantly swayable in said substrate, said first header having terminal end portions of a multiplicity of fibers sealingly secured in said first header, and said second header having opposed terminal end portions of said fibers sealingly secured in said second header, essentially all ends of said fibers being open so as to discharge permeate through said headers;

said bundle comprising a multiplicity of fibers sealingly secured in closely-spaced-apart profusion and sealed with potting resin;

liquid collection means secured in fluid-tight open communication with permeate-discharging faces of said headers; means for mounting said headers and liquid collection means for operation in said substrate;

said gas-distribution means, located within a zone directly beneath said skein, having through-passages therein adapted to have sufficient gas flowed therethrough to generate enough bubbles flowing through said skein and around said fibers, so as to keep surfaces of said fibers awash with bubbles; and, means for withdrawing said permeate.

11. The gas-scrubbed assembly of claim 10 wherein said through-passages in said gas-distribution means generate bubbles having an average diameter in the range from about 1 mm to about 50 mm, measured relatively close to said fibers, which bubbles contact said fibers, maintain their buoyancy, and maintain said fibers, outer surfaces essentially free from build-up of deposits of said particulate matter.

12. The gas-scrubbed assembly of claim 11 wherein said through-passages in said gas-distribution means generate bubbles in the size range from 1 mm to 25 mm in relatively close proximity, in the range from 1 cm to about 50 cm, to said fibers, and the flow rate of said gas is in the range from about 0.3 m$^3$/day/m$^2$ to 400 m$^3$/day/m$^2$ so as to maintain essentially the entire length of each fiber in the skein awash with bubbles.

13. The gas-scrubbed assembly of claim 11 wherein said fibers have pores from 0.001 $\mu$m-0.1 $\mu$m, said gas is an oxygen-containing gas, and said particulate matter comprises biologically active microorganisms growing in said substrate.

14. The gas-scrubbed assembly of claim 11 wherein said particulate matter comprises finely divided inorganic particles.

15. A system for withdrawing permeate from a multicomponent liquid substrate having particulate matter suspended therein, with a gas-scrubbed assembly comprising a frameless array of hollow fiber membranes (or "fibers") in combination with a gas-distribution means, said system comprising, means for providing an alterative to a conventional module having plural individual arrays therewithin, including, a reservoir for a volume of at least 100 liters of said substrate from which a permeate is to be withdrawn;

a pair of headers adapted to be mounted in spaced-apart relationship within said substrate without being confined in a modular shell, a first header having terminal end portions of a multiplicity of fibers secured therein, and a second header having opposed terminal end portions of said fibers secured therein, essentially all ends of said fibers being open so as to discharge permeate through said headers, at least one header being disposed below a horizontal plane through the horizontal center plane of said one header;

said fibers formed from a material selected from the group consisting of an inorganic material and an organic synthetic resinous material, and swayably buoyantly deployed in a body of said substrate, said fibers together having a surface area in excess of 10 m$^2$, each fiber having a length $>0.5$ m and sufficiently greater than the direct distance between said first and second headers, so as to present, when said skein is deployed, a generally arcuate configuration above a plane through the horizontal centerline of a headers;

collection means for collecting said permeate;

means for mounting said spaced-apart headers in open fluid communication with said collection means;

means for withdrawing said permeate; and, said gas-distribution means disposed within a zone beneath said skein, and adapted to generate bubbles which flow upwardly through said skein, whereby said fibers are kept awash in bubbles and resist the build-up of said particulate matter on the surfaces of said fibers.

16. The system of claim 15 wherein said through-passages in said gas-distribution means generate bubbles having an average diameter in the range from about 1 mm to about 50 mm, in relatively close proximity to said fibers so as to maintain essentially the entire length of each fiber in the skein awash with bubbles and essentially free from build-up of said particulate matter; and, said particulate matter is selected from the group consisting of microorganisms growing in said substrate, and finely divided inorganic particles suspended therein.

17. The system of claim 16 wherein each said header is a mass of solid synthetic resinous material in which at least 100 terminal end portions are potted; each said hollow fiber has an outside diameter in the range from about 20 $\mu$m to about 3 mm, and a wall thickness in the range from about 5 $\mu$m to about 1 mm; and said terminal end portions of said fibers are potted within said resinous material to a depth in the range from about 1 cm to about 5 cm.

18. The system of claim 17 wherein said arcuate configuration is generally parabolic, and said means for withdrawing permeate is a pump incapable of inducing a vacuum of 75 cm of Hg on the suction side.

19. A process for maintaining the outer surfaces of hollow fiber membranes essentially free from a build-up of deposits of particulate material while separating a permeate from a multicomponent liquid substrate in a reservoir, said process comprising, providing an alternative to a conventional module having plural individual arrays therewithin, by submerging a frameless array of fibers deployed as a skein within said substrate unconfined in a modular shell, said fibers being securely held in laterally opposed, spaced-apart first and second headers, said fibers having a transmembrane pressure differential in the range from about 0.7 kPa (0.1 psi) to about 345 kPa (50 psi), a total surface area $>1$ m$^2$, and a length sufficiently greater than the direct distance between said first and second headers, so as to present said skein in a buoyantly swayable generally arcuate fiber configuration above a horizontal plane through the horizontal center-line of a header;

mounting said headers in fluid-tight open communication with collection means to collect said permeate;

flowing a fiber-cleansing gas through a gas-distribution means proximately disposed relative to said skein, within a zone directly beneath said skein, and contacting surfaces of said fibers with sufficient physical impact of bubbles of said gas to maintain essentially the entire length of each fiber in said skein awash with bubbles and essentially free from said build-up;

maintaining an essentially constant flux through said fibers substantially the same as an equilibrium flux initially obtained after commencing operation of said process;

collecting said permeate in said collection means; and, withdrawing said permeate.

20. The process of claim 19 wherein each said hollow fiber has an outside diameter in the range from about 20 μm to about mm, and a wall thickness in the range from about 5 μm to about 1 mm; each said header is formed from a mass of thermosetting synthetic resinous material; terminal end portions of said fibers are potted within said resinous material to a depth in the range from about 1 cm to about 5 cm; and, said gas-distribution means generates bubbles having an average diameter in the range from about 1 mm to about 50 mm.

21. The process of claim 20 comprising, flowing said gas at a flow rate in the range from about 10 m$^3$/day/m$^2$ to 200 m$^3$/day/m$^2$, and, withdrawing said permeate using a transmembrane pressure differential induced by gravity.

22. The process of claim 21 comprising, flowing said gas at a flow rate in the range from about 10 m$^3$/day/m$^2$ to 200 m$^3$/day/m$^2$, and, withdrawing said permeate with a pump incapable of inducing a vacuum of 75 cm of Hg on its suction side.

23. The process of claim 20 comprising, flowing said gas at a flow rate in the range from about 10 m$^3$/day/m$^2$ to 200 m$^3$/day/m$^2$, and, withdrawing said permeate with a vacuum pump capable of inducing a vacuum greater than 75 cm of Hg on its suction side.

24. The process of claim 20 wherein said particulate matter is selected from the group consisting of microorganisms and finely divided inorganic particles, and said arcuate configuration is generally parabolic.

* * * * *

UNITED STATES PATENT AND TRADEMARK OFFICE
CERTIFICATE OF CORRECTION

PATENT NO. : 5,248,424  
APPLICATION NO. : 07/977601  
DATED : September 28, 1993  
INVENTOR(S) : Cote et al.

Page 1 of 1

It is certified that error appears in the above-identified patent and that said Letters Patent is hereby corrected as shown below:

In the drawings, Sheet 12, Figure 9A, should appear as follows:

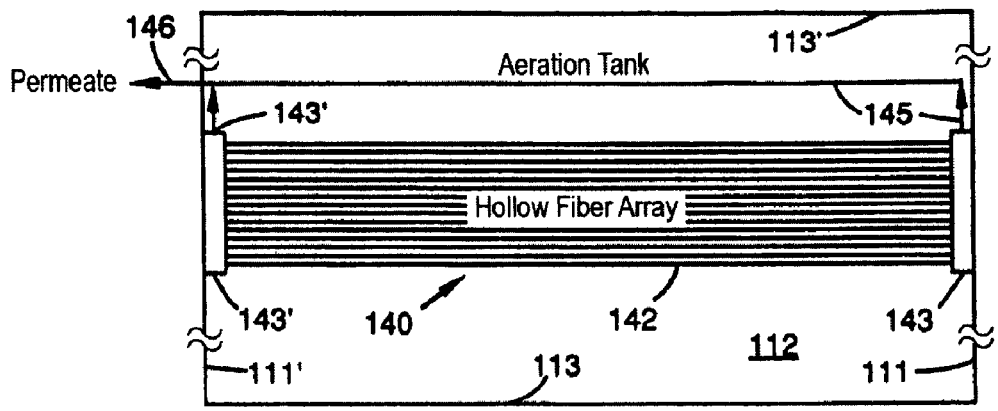

Figure 9A

Col 29, line 56, delete "fibers," and subtitute --fibers'--.

Col. 32, line 11, delete "mm" and substitute --3 mm--.

Signed and Sealed this

Tenth Day of October, 2006

JON W. DUDAS  
*Director of the United States Patent and Trademark Office*